(12) United States Patent
Yokose et al.

(10) Patent No.: US 11,639,940 B2
(45) Date of Patent: May 2, 2023

(54) METHOD FOR DETERMINING SENSITIVITY OF CYCLIN-DEPENDENT KINASE 4/6 INHIBITOR

(71) Applicant: SYSMEX CORPORATION, Kobe (JP)

(72) Inventors: Noriko Yokose, Kobe (JP); Kenta Noda, Kobe (JP)

(73) Assignee: SYSMEX CORPORATION, Kobe (JP)

(*) Notice: Subject to any disclaimer, the term of this patent is extended or adjusted under 35 U.S.C. 154(b) by 392 days.

(21) Appl. No.: 16/832,569

(22) Filed: Mar. 27, 2020

(65) Prior Publication Data

US 2020/0309787 A1 Oct. 1, 2020

(30) Foreign Application Priority Data

Mar. 28, 2019 (JP) .............................. JP2019-063185

(51) Int. Cl.
| | |
|---|---|
| G01N 1/00 | (2006.01) |
| G01N 33/68 | (2006.01) |
| G01N 33/574 | (2006.01) |
| G01N 33/573 | (2006.01) |
| C12Q 1/48 | (2006.01) |
| G01N 33/15 | (2006.01) |
| C07K 16/30 | (2006.01) |
| G01N 33/487 | (2006.01) |

(52) U.S. Cl.
CPC ......... *G01N 33/6863* (2013.01); *C12Q 1/485* (2013.01); *G01N 33/573* (2013.01); *G01N 33/57407* (2013.01); *G01N 33/57415* (2013.01); *C07K 16/30* (2013.01); *G01N 33/15* (2013.01); *G01N 33/487* (2013.01); *G01N 2333/90* (2013.01); *G01N 2333/91205* (2013.01)

(58) Field of Classification Search
CPC .................................................. G01N 33/6863
USPC ........................................................ 424/94.5
See application file for complete search history.

(56) References Cited

FOREIGN PATENT DOCUMENTS

| EP | 3458604 A1 | 3/2019 |
|---|---|---|
| JP | 2007-006682 A | 1/2007 |
| JP | 2010-227058 A | 10/2010 |
| WO | 2005/116241 A1 | 12/2005 |
| WO | 2015/066452 A2 | 5/2015 |
| WO | 2017/198685 A1 | 11/2017 |

OTHER PUBLICATIONS

Sheppard et al (Clin Cancer Res, 2013, 19(19): 5320-5328).*
Pernas et al (Ther Adv Med Oncol, 2018, 10: 1-15).*
The Communication pursuant to Article 94(3) EPC dated Jun. 2, 2021 in a counterpart European patent application No. 20166115.4.
The extended European search report dated Oct. 14, 2020 in a counterpart European patent application No. 20166115.4.
Robert Roskoski Jr., "Cyclin-dependent protein kinase inhibitors including palbociclib as anticancer drugs", Pharmacological Research, 2016, pp. 249-275, vol. 107.
Priyank Patel et al., "Dual Inhibition of CDK4 and CDK2 via Targeting p27 Tyrosine Phosphorylation Induces a Potent and Durable Response in Breast Cancer Cells", Molecular Cancer Research, Mar. 2018;pp. 361-377, 16(3).
Maria Teresa Herrera-Abreu et al., "Early Adaption and Acquired Resistance to CDK4/6 Inhibition in Estrogen Receptor-Positive Breast Cancer", Cancer Research, Apr. 15, 2016, pp. 2301-2313, 76(8).
Valerie M. Jansen et al. "Kinome-Wide RNS Interference Screen Reveals a Role for PDK1 in Acquired Resistance to CDK4/6 Inhibition in ER-Positive Breast Cancer", Cancer Research, May 1, 2017, pp. 2488-2499, 77(9).
Uzma S. Asghar et al., "Single-Cell Dynamics Determines Response to CDK4/6 Inhibition in Triple-Negative Breast Cancers", Clinical Cancer Research, Sep. 15, 2017, pp. 5561-5572, 23(18).
Y. Katsumi et al., "Sensitivity of malignant rhabdoid tumor cell lines to PD 0332991 is inversely correlated with p16 expression", Biochemical and Biophysical Research Communications, vol. 413, No. 1, Aug. 17, 2011, pp. 62-68.
JGH Van Nes et al., "Validation study of the prognostic value of cyclin-dependent kinase(CDK)-based risk in Caucasian breast cancer patients", British Journal of Cancer, vol. 100, No. 3, Jan. 20, 2009, pp. 494-500.
C.M. Cover et al., "Indole-3-Carbinol and Tamoxifen Cooperate to Arrest the Cell Cycle of MCF-7 Human Breast Cancer Cells", Cancer Research, American Association for Cancer Research, AACR Annual Meeting 2018; Apr. 14-18, 2018; Chicago, IL, vol. 59, Mar. 15, 1999, pp. 1244-1251.
A. Nemoto et al., "Specific Antileukemic Activity of PD0332991, a CDK4/6 Inhibitor, against Philadelphia Chromosome-Positive Lymphoid Leukemia", Molecular Cancer Therapeutics, vol. 15, No. 1, Jan. 1, 2016, pp. 94-105.
The partial European search report dated Jul. 13, 2020 in a counterpart European patent application No. 20166115.4.
Eric Raspéet al: "CDK4 phosphorylation status and a linked gene expression profile predict sensitivity to palbociclib", EMBO Molecular Medicine, 2017, vol. 9, No. 8, pp. 1052-1066.
Uzma Asghar et al: "The history and future of targeting cyclin-dependent kinases in cancer therapy", Nature Reviews Drug Discovery, 2015, vol. 14, No. 2, pp. 130-146.
The Japanese Office Action dated Jan. 24, 2023 in a counterpart Japanese patent application No. 2019-063185.

* cited by examiner

*Primary Examiner* — Sean E Aeder
(74) *Attorney, Agent, or Firm* — Sughrue Mion, PLLC

(57) ABSTRACT

Disclosed is a method for determining sensitivity to a CDK4/6 inhibitor, comprising the steps of: comparing a value based on activity of at least one CDK selected from CDK4 and CDK6 in a sample collected from a subject, with a threshold level corresponding to the CDK, and determining that the subject is insensitive to the CDK4/6 inhibitor when the value based on the CDK activity is less than the threshold level.

12 Claims, 9 Drawing Sheets

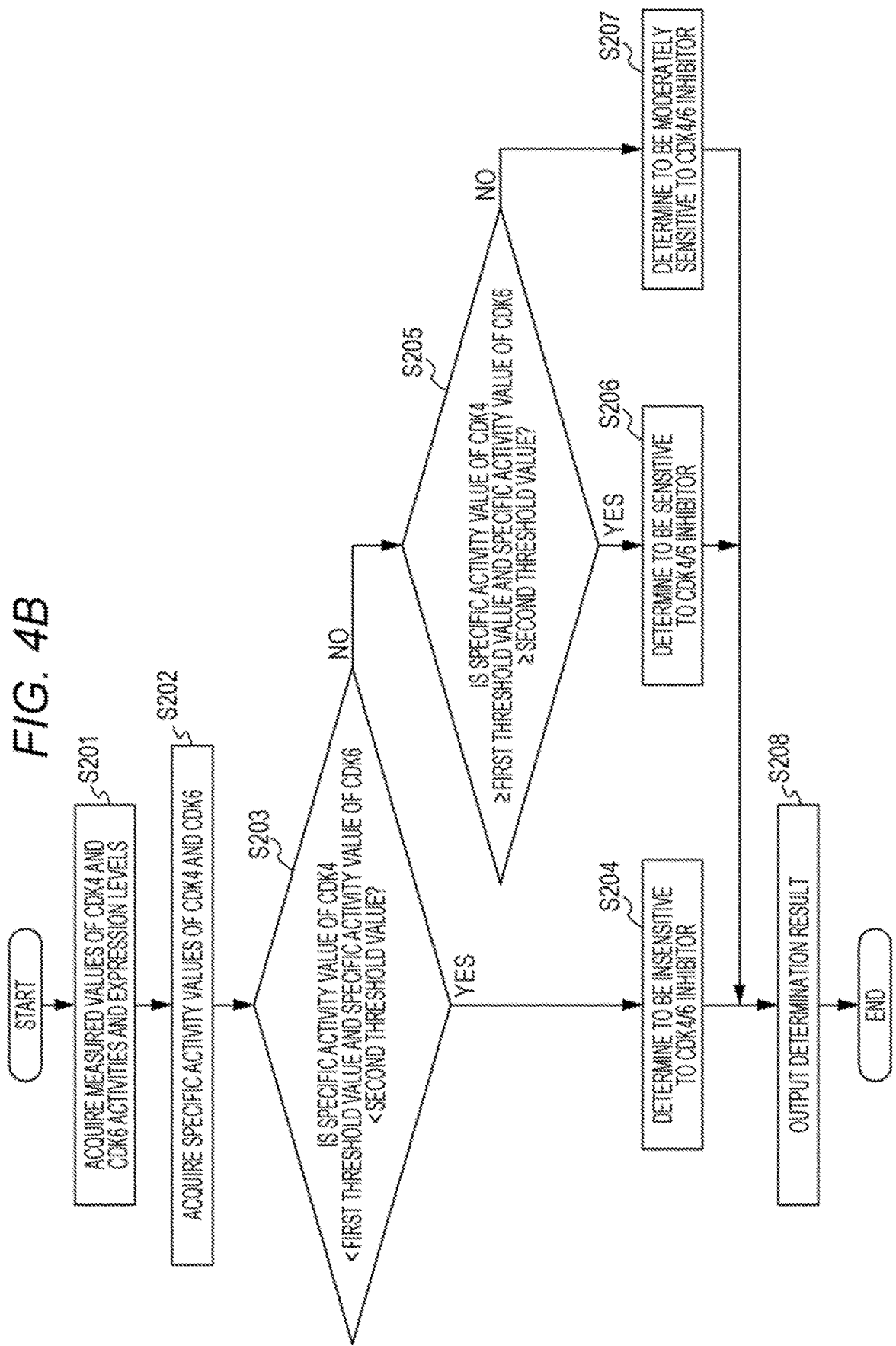

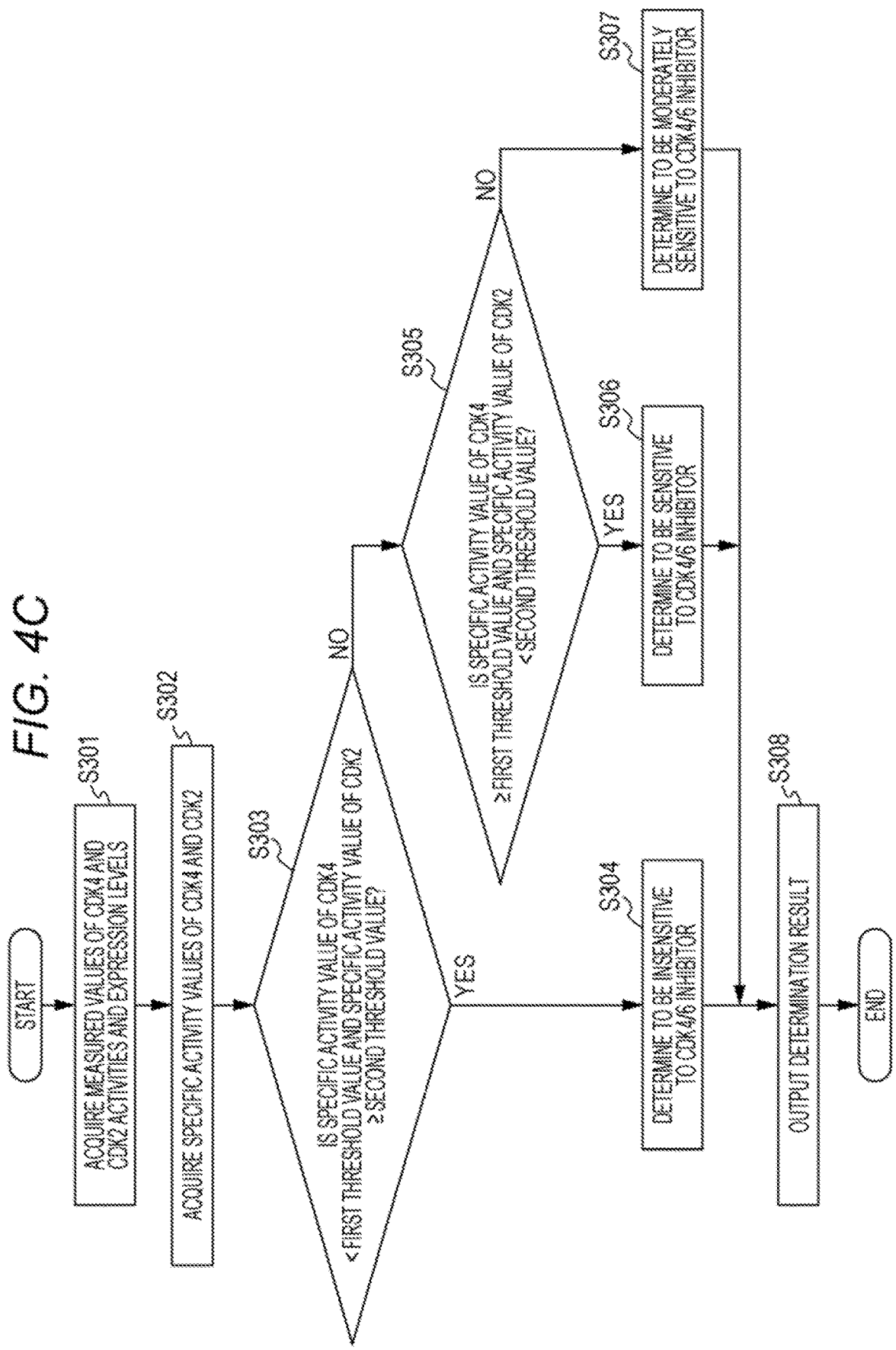

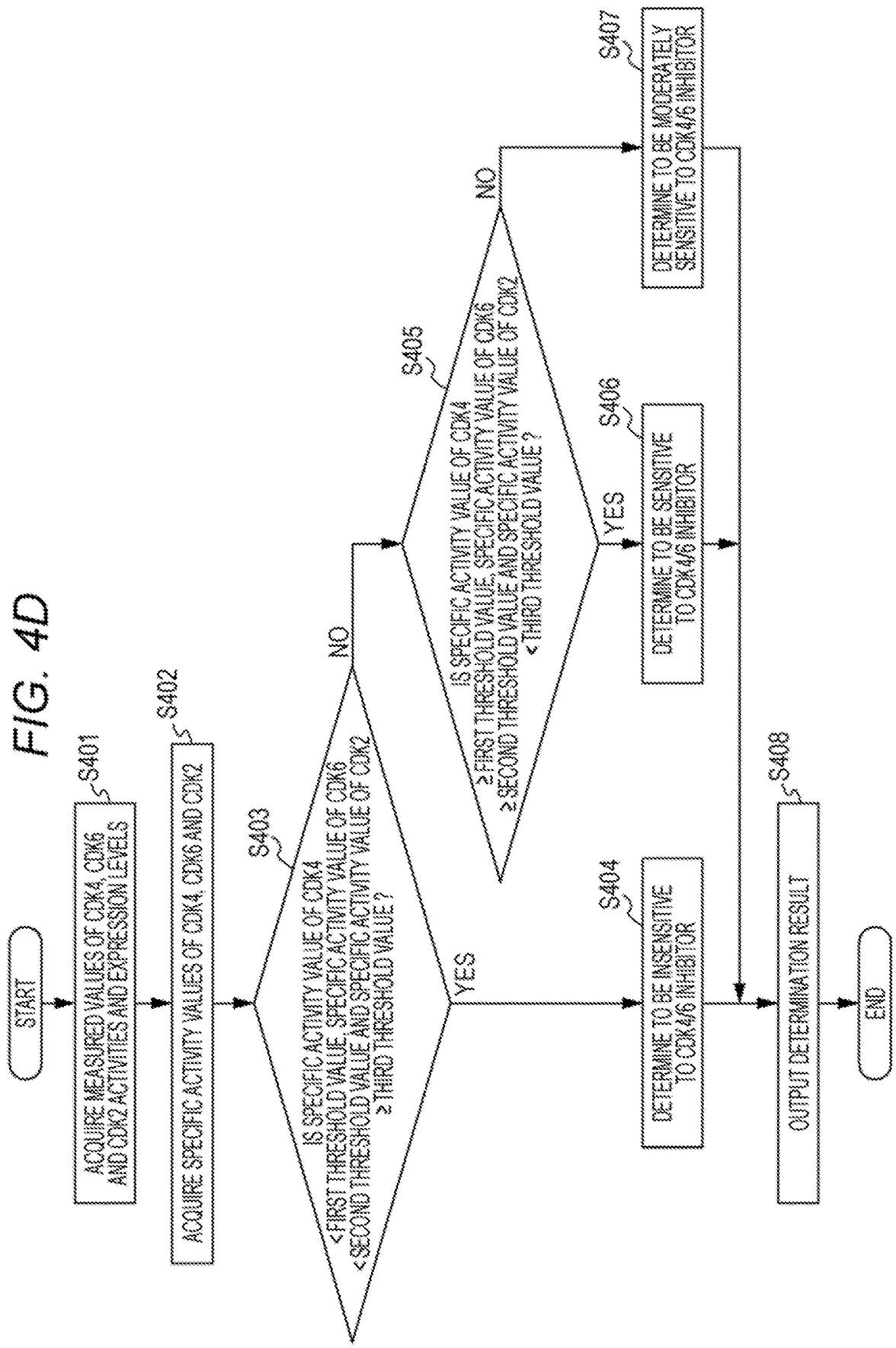

METHOD FOR DETERMINING SENSITIVITY OF CYCLIN-DEPENDENT KINASE 4/6 INHIBITOR

CROSS REFERENCE TO RELATED APPLICATIONS

This application claims priority from prior Japanese Patent Application No. 2019-063185, filed on Mar. 28, 2019, entitled "Method, reagent kit, apparatus and computer program for determining sensitivity of cyclin-dependent kinase 4/6 inhibitor", the entire contents of which are incorporated herein by reference.

TECHNICAL FIELD

The present invention relates to a method for determining sensitivity of a cyclin dependent kinase (CDK) 4/6 inhibitor. The present invention also relates to a reagent kit, an apparatus and a computer program for determining sensitivity to a CDK4/6 inhibitor.

BACKGROUND

In normal cells, cell cycle is controlled so that disordered cell division does not occur. However, in cancer cells, involvement of CDK4 and CDK6 makes it impossible to control the cell cycle, resulting in unlimited cell proliferation. The CDK4/6 inhibitor inhibits activity of a complex of CDK4 or CDK6 and cyclin D, thereby stopping progress of the cell cycle and suppressing growth of cancer cells. Currently, the CDK4/6 inhibitor is approved as a therapeutic agent for inoperable or recurrent breast cancer.

Patel P. et al., Dual Inhibition of CDK4 and CDK2 via Targeting p27 Tyrosine Phosphorylation Induces a Potent and Durable Response in Breast Cancer Cells, Mol Cancer Res, 2018, vol. 16, p. 361-377 describes that, in treatment of breast cancer with CDK4/6 inhibitors such as palbociclib, regarding a problem that cancer cells acquire resistance to the inhibitor, CDK2 rescues palbociclib-suppressed breast cancer cells by compensating for a decrease in CDK4 activity.

In order to treat cancer more effectively, it is important to select an optimal treatment for each patient. For example, when choosing treatment with a CDK4/6 inhibitor, it is desirable to be able to predict whether a patient will be sensitive to a CDK4/6 inhibitor. Prediction of sensitivity to a CDK4/6 inhibitor is also useful in determining whether or not to continue treatment with a CDK4/6 inhibitor. An object of the present invention is to provide a method capable of determining sensitivity of a subject to a CDK4/6 inhibitor.

SUMMARY OF THE INVENTION

The scope of the present invention is defined solely by the appended claims, and is not affected to any degree by the statements within this summary.

The present invention provides a method for determining sensitivity to a CDK4/6 inhibitor, including the steps of: comparing a value based on activity of at least one CDK selected from CDK4 and CDK6 in a sample collected from a subject, with a threshold level corresponding to the CDK, and determining that the subject is insensitive to the CDK4/6 inhibitor when the value based on the CDK activity is less than the threshold level.

The present invention provides a method for determining sensitivity to a CDK4/6 inhibitor, including the steps of: acquiring a first specific activity value which is specific activity of first CDK in a first aliquot of a sample collected from a subject, and a second specific activity value which is specific activity of first CDK in a second aliquot of the sample, and determining that the subject is insensitive to the CDK4/6 inhibitor when a ratio value of the second specific activity value to the first specific activity value is less than a predetermined threshold level, or a ratio value of the first specific activity value to the second specific activity value is greater than or equal to the predetermined threshold level, wherein the first CDK is CDK4 or CDK6, the first aliquot is an aliquot not treated with the CDK4/6 inhibitor, and the second aliquot is an aliquot treated in vitro with the CDK4/6 inhibitor.

The present invention is a method for determining sensitivity to a CDK4/6 inhibitor of a subject who has been administered the CDK4/6 inhibitor, including the steps of: acquiring a first specific activity value which is specific activity of first CDK in a first sample, and a second specific activity value which is specific activity of first CDK in a second sample, and determining that the subject is insensitive to the CDK4/6 inhibitor when a ratio value of the second specific activity value to the first specific activity value is less than a predetermined threshold level, or a ratio value of the first specific activity value to the second specific activity value is greater than or equal to the predetermined threshold level, wherein the first CDK is CDK4 or CDK6, the first sample is a sample collected from the subject before administration of the CDK4/6 inhibitor, and the second sample is a sample collected from the subject after administration of the CDK4/6 inhibitor.

The present invention provides a reagent kit for use in the method including a capture substance that binds to at least one CDK selected from CDK4 and CDK6, and a substrate for the CDK.

The present invention provides an apparatus for determining sensitivity to a CDK4/6 inhibitor, including a computer containing a processor and a memory under control of the processor, the memory being recorded with a computer program for making the computer execute the steps of comparing a value based on activity of at least one CDK selected from CDK4 and CDK6 in a sample collected from a subject, with a threshold level corresponding to the CDK, and determining that the subject is insensitive to the CDK4/6 inhibitor when the value based on the CDK activity is less than the threshold level.

The present invention provides a computer program for determining sensitivity to a CDK4/6 inhibitor, recorded on a computer-readable medium, the computer program being a computer program for making the computer execute the steps of acquiring a value based on activity of at least one CDK selected from CDK4 and CDK6 in a sample collected from a subject, comparing the value based on the CDK activity with a threshold level corresponding to the CDK, and determining that the subject is insensitive to the CDK4/6 inhibitor when the value based on the CDK activity is less than the threshold level.

According to the present invention, sensitivity of a subject to a CDK4/6 inhibitor can be determined.

BRIEF DESCRIPTION OF THE DRAWINGS

FIG. 4B is a flowchart for determining sensitivity to a CDK4/6 inhibitor using the determination apparatus of the present embodiment;

FIG. 4C is a flowchart for determining sensitivity to a CDK4/6 inhibitor using the determination apparatus of the present embodiment;

FIG. 4D is a flowchart for determining sensitivity to a CDK4/6 inhibitor using the determination apparatus of the present embodiment;

DETAILED DESCRIPTION OF THE PREFERRED EMBODIMENTS

Figure 1A:
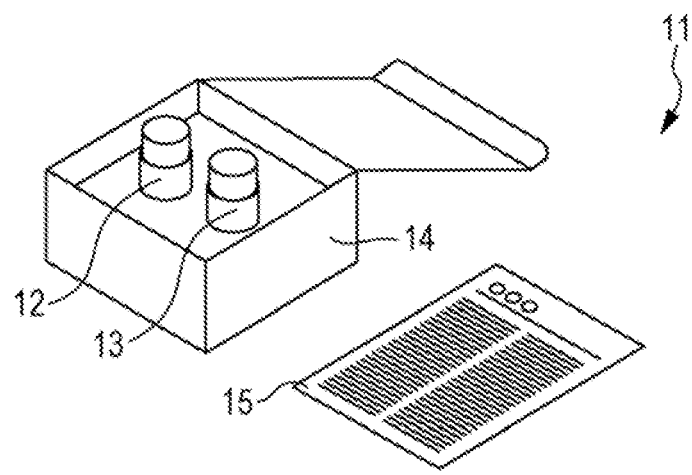
FIG. 1A is a schematic diagram showing an example of the reagent kit of the present embodiment.

As used herein, when it is simply described as "CDK" without referring to which CDK, the term "CDK" includes CDK2, CDK4, and CDK6.

[1. Method for Determining Sensitivity to CDK4/6 Inhibitor]

In the method for determining sensitivity to a CDK4/6 inhibitor of the present embodiment (hereinafter, also referred to as "determination method"), a value based on activity of at least one CDK selected from CDK4 and CDK6 in a sample collected from a subject is compared with a threshold level corresponding to the CDK, and sensitivity of the subject to a CDK4/6 inhibitor is determined based on the comparison result.

(CDK4/6 Inhibitor)

The CDK4/6 inhibitor is a compound that specifically inhibits at least one of CDK4 and CDK6, or a preparation containing the compound as an active ingredient. Examples of such inhibitors include palbociclib, abemaciclib, ribociclib, or trilaciclib, and the like, but are not limited thereto. The determination method of the present embodiment is particularly suitable for determining sensitivity of palbociclib.

(Subject and Sample)

The subject may be any one who is considering starting, continuing or stopping treatment with a CDK4/6 inhibitor. Such subjects include cancer patients. The type of cancer is not particularly limited, but a cancer that can be effectively treated with a CDK4/6 inhibitor is preferable. Examples of the type of cancer include breast cancer, head and neck cancer, non-small cell lung cancer, and the like. The determination method of the present embodiment is particularly suitable for breast cancer patients.

The subject may be a breast cancer patient who has undergone treatment with a CDK4/6 inhibitor. Even in patients who respond to CDK4/6 inhibitors, resistance may be acquired by continuous administration of CDK4/6 inhibitors. That is, even patients who were sensitive to the CDK4/6 inhibitor at the beginning of treatment may become insensitive due to acquired resistance. According to the method of the present embodiment, it is possible to determine whether a breast cancer patient who has undergone treatment with a CDK4/6 inhibitor has developed resistance to the CDK4/6 inhibitor. The subject may be a cancer patient (especially a breast cancer patient) who has undergone treatment other than CDK4/6 inhibitors. Such treatments include surgery, irradiation, chemotherapy, hormonal therapy and combinations thereof, and the like.

The sample collected from the subject is not particularly limited as long as it contains CDK of the subject. In the present embodiment, the collected sample preferably contains cells or tissues of the subject. When the subject is a cancer patient, the collected sample preferably contains cancer cells or tumor tissues of the subject. Examples of such samples include cells or tissues collected by fine needle aspiration, tissues collected by surgery or biopsy, and the like. In a preferred embodiment, the collected sample is a breast cancer cell or breast cancer tissue collected by fine needle aspiration from a breast cancer patient, a breast cancer tissue collected by surgery or biopsy, or the like.

In the present embodiment, it is preferable to use a liquid sample prepared from cells or tissues collected from a subject as the sample. The method for preparing a liquid sample containing protein such as CDK from cells or tissues is known per se in the art. For example, a liquid sample containing CDK can be obtained by solubilizing cells or tissues by mixing the cells or tissues with a buffer solution containing a suitable surfactant. When the liquid sample contains insoluble contaminants such as crushed cells or tissues, the contaminants may be removed by centrifugation, filtration, or the like.

The surfactant is not particularly limited, and can be used in a range that does not inhibit kinase activity of CDK. Examples of the surfactant include polyoxyalkylphenyl ether (for example, NP-40, Triton (trademark) X-100, or the like), polysorbate (for example, Tween (trademark) 20 or the like), deoxycholic acid, CHAPS, and the like. The buffer solution is not particularly limited as long as it can maintain a pH suitable for the kinase activity of CDK (usually pH 6 to 8, preferably pH 7 to 7.8). Such buffer solutions include Tris-HCl, HEPES, PIPES, and the like.

A reagent for preventing degradation or denaturation of CDK may be added to the buffer solution. Such reagents include protease inhibitors and the like. Examples of the protease inhibitor include ethylenediaminetetraacetic acid (EDTA), phenylmethylsulfonyl fluoride (PMSF), commercially available protease inhibitor cocktails, and the like. A phosphatase inhibitor such as sodium fluoride or sodium orthovanadate may be added to the buffer solution.

(Value Based on CDK Activity)

The present inventors have found that, in various cancer cell lines, the values based on CDK4 and CDK6 activities differ depending on sensitivity of each cancer cell line to a CDK4/6 inhibitor. That is, the present inventors have found that the values based on the CDK4 and CDK6 activities are parameters for determining sensitivity to a CDK4/6 inhibitor. The value based on the CDK activity is a value acquired using a measured value of CDK activity (kinase activity) and a measured value of expression level of the CDK. Examples of such values include a ratio, product, sum, and difference of the measured value of CDK activity and the measured value of expression level of the CDK, and the like.

The measured value of activity and expression level of each CDK can be obtained by measuring the activity and expression level of each CDK in cells or tissues collected from a subject. In a preferred embodiment, the measured value of activity and the measured value of expression level of each CDK are obtained by measuring the activity and expression level of each CDK in a liquid sample prepared from cells or tissues collected from a subject.

In a preferred embodiment, the value based on the CDK activity is a value obtained by normalizing the measured value of CDK activity with the measured value of expression level of the CDK. Examples of such values based on the CDK activities include specific activity values of CDK. Each of specific activity values of CDK4 and CDK6 can be calculated by the following equation. Alternatively, a value (for example, a product, ratio, sum, difference, or the like) acquired using a value calculated by the following equation and a predetermined constant or coefficient may be used as the specific activity values of CDK4 and 6.

[Specific activity value of CDK4]=[Measured value of CDK4 activity]/[Measured value of expression level of CDK4]

[Specific activity value of CDK6]=[Measured value of CDK6 activity]/[Measured value of expression level of CDK6]

In a more preferred embodiment, the value based on the CDK activity is a value that indicates how much the specific activity of CDK changes when a sample collected from a subject is treated in vitro with a CDK4/6 inhibitor as compared to when untreated. The phrase "treated in vitro with a CDK4/6 inhibitor" intends that the CDK4/6 inhibitor was acted on a sample collected from a subject, that is, a sample separated from a living body. Such values can be acquired from the activity and expression level of CDK obtained from a sample treated in vitro with a CDK4/6 inhibitor, and the activity and expression level of CDK obtained from a sample not treated with a CDK4/6 inhibitor. For example, the value based on the CDK activity may be a ratio value of the specific activity value of CDK in a sample treated with a CDK4/6 inhibitor to the specific activity value of CDK in a sample not treated with a CDK4/6 inhibitor. Each of ratio values of specific activities of CDK4 and CDK6 can be calculated by the following equation. Alternatively, a value (for example, a product, ratio, sum, difference, or the like) acquired using a value calculated by the following equation and a predetermined constant or coefficient may be used as the ratio values of specific activities of CDK4 and 6.

[Ratio value of specific activity of CDK4]=[Specific activity value of CDK4 of sample treated with CDK4/6 inhibitor]/[Specific activity value of CDK4 of sample not treated with CDK4/6 inhibitor]

[Ratio value of specific activity of CDK6]=[Specific activity value of CDK6 of sample treated with CDK4/6 inhibitor]/[Specific activity value of CDK6 of sample not treated with CDK4/6 inhibitor]

The ratio value can be acquired, for example, as follows. Cells or tissues collected from a subject are divided into two, and one is added with a CDK4/6 inhibitor, the other is not added with a CDK4/6 inhibitor, then both are incubated. The incubation time is 6 hours or more, preferably 12 hours or more, and more preferably 24 hours or more, and 72 hours or less, preferably 60 hours or less, and more preferably 48 hours or less. The final concentration of the CDK4/6 inhibitor is 10 nM or more, preferably 100 nM or more, and more preferably 500 nM or more, and 10000 nM or less, preferably 5000 nM or less, and more preferably 1000 nM or less. After incubation, a liquid sample is prepared from the cells or tissue. The activity and expression level of CDK in the liquid sample are measured to acquire the specific activity value of CDK. Then, the specific activity value of CDK in a sample treated with a CDK4/6 inhibitor is divided by the specific activity value of CDK in a sample not treated with a CDK4/6 inhibitor to obtain a ratio value.

(Measurement of CDK Activity)

In the present embodiment, the method for measuring CDK activity is not particularly limited as long as a value reflecting a kinase activity of CDK in the sample can be acquired. Preferred sample is a liquid sample prepared from cells or tissues collected from a subject. In a preferred embodiment, the method for measuring CDK activity is a method including the steps of phosphorylating a substrate with CDK and measuring the amount of phosphorylated substrate. Such a measuring method can be selected from known in vitro kinase assays using a substrate for CDK. In the in vitro kinase assay, the amount of the substrate phosphorylated by a kinase is measured, and the obtained measured value is acquired as the value reflecting a kinase activity. A commercially available kinase assay kit may be used for the measurement.

The substrates for CDK4 and CDK6 are not particularly limited, and can be selected from known CDK substrates such as retinoblastoma (RB) protein. A commercially available CDK substrate may be used. In the present embodiment, the substrate is not limited to protein, and may be an oligopeptide. As a substrate for the oligopeptide, for example, a substrate peptide described in EP 3 404 038 A1 (herein incorporated by reference) is preferable. This substrate peptide has a high reactivity to CDK, and especially has a higher specificity for CDK4 and CDK6.

A tag or the like may be added to the substrate, as necessary. The tag attached to the substrate is useful for capturing or recovering the substrate. Examples of the tag include a biotin tag, a His tag, a FLAG tag, a Halo tag, an MBP tag, an HA tag, a Myc tag, a V5 tag, a PA tag, and the like. In the present embodiment, it is preferable to use a substrate to which a biotin tag has been added.

In the present embodiment, it is preferable to use a substrate, a capture substance that binds to CDK4, and a solid phase to measure activity of CDK4 in the liquid sample. It is preferable to use a substrate, a capture substance that binds to CDK6, and a solid phase to measure activity of CDK6 in the liquid sample. Briefly describing a measurement procedure, first, CDK4 or 6 immobilized on a solid phase via a capture substance is brought into contact with a substrate to perform a phosphorylation reaction of the substrate with CDK4 or 6. Then, an activity value of CDK4 or 6 is obtained by measuring the amount of the generated phosphorylated substrate. Hereinafter, the case where the CDK4 activity is measured will be described as an example, but the CDK6 activity can be similarly measured by using a capture substance that binds to CDK6.

First, a complex containing CDK4 and a capture substance that binds to CDK4 is formed on a solid phase. The complex can be formed by mixing a liquid sample, a capture substance that binds to CDK4, and a solid phase. The order of mixing is not particularly limited. Alternatively, a solid phase in which a capture substance that binds to CDK4 is immobilized in advance may be used. That is, a liquid sample and a solid phase on which a capture substance that binds to CDK4 is immobilized are mixed so that the complex can be formed on the solid phase. Since CDK4 exhibits activity by binding to cyclin corresponding to CDK4, it is considered that, in the liquid sample, the complex containing CDK4, the capture substance that binds to CDK4, and cyclin D1, D2 or D3 is formed on the solid phase. The same applies to CDK6.

The capture substance that binds to CDK4 is a substance that specifically binds to CDK4, and refers to a substance for immobilizing CDK4 on a solid phase. The capture substance that binds to CDK6 is a substance that specifically binds to CDK6, and refers to a substance for immobilizing CDK6 on a solid phase. Examples of such capture substances include antibodies, aptamers, and the like. The antibody may be any of monoclonal antibodies, polyclonal antibodies, and fragments thereof (for example, Fab, F(ab')$_2$, Fab', and the like). Preferably, it is a monoclonal antibody. In the present embodiment, the substance that specifically binds to CDK4 is preferably an anti-CDK4 antibody, and the substance that specifically binds to CDK6 is preferably an anti-CDK6 antibody. The anti-CDK4 and anti-CDK6 antibodies are commercially available and generally available.

The solid phase used for the phosphorylation reaction may be any insoluble carrier capable of immobilizing a capture substance. The capture substance that specifically binds to CDK4 is immobilized on the solid phase, whereby CDK4 is captured on the solid phase via the capture substance. The mode of immobilization of the capture substance on the solid phase is not particularly limited. For example, the capture substance and the solid phase may be bound directly, or the capture substance and the solid phase may be indirectly bound via another substance. The direct binding includes physical adsorption and the like. The indirect binding includes binding via a combination of a binding substance and a binding partner. The combinations of a binding substance and a binding partner are known, and examples thereof include combinations of biotins (including biotin analogs such as biotin and desthiobiotin) and avidins (including avidin analogs such as avidin and streptavidin), combinations of hapten and an anti-hapten antibody, and the like. As the combination of a hapten and an anti-hapten antibody, a 2,4-dinitrophenyl (DNP) group and an anti-DNP antibody are particularly preferable. For example, by modifying a capture substance with a DNP group in advance and immobilizing an anti-DNP antibody on a solid phase in advance, the capture substance can be bound to the solid phase via a binding between the DNP group and the anti-DNP antibody. When the capture substance is an antibody, a solid phase to which protein A or G is immobilized may be used.

When a tag is added to the substrate, it is preferable to use a binding substance or a binding partner other than the tag. For example, when a biotin tag is added to the substrate, the capture substance and the solid phase preferably bind via a combination of a binding substance and a binding partner other than a combination of biotins and avidins.

The material of the solid phase is not particularly limited, and it can be selected from, for example, organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, and the like), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include particles, membranes, microplates, microtubes, test tubes, and the like. Among them, particles are preferable, and magnetic particles are particularly preferable.

After the formation of the complex, supernatant is removed, and a solid phase capturing the complex is recovered. Since the supernatant contains unreacted free components, the step of recovering the complex corresponds to B/F (Bound/Free) separation. The unreacted free component refers to a component not constituting a complex. Examples thereof include capture substances that did not bind to CDK4 and the like. Means for recovering the solid phase capturing the complex is not particularly limited. For example, when the solid phase is particles, only the solid phase can be recovered by removing the supernatant by precipitating the solid phase by centrifugation. When the solid phase is a container such as a microplate or a microtube, only the solid phase can be recovered by removing the supernatant. When the solid phase is magnetic particles, only the solid phase can be recovered by magnetically constraining the magnetic particles with a magnet and aspirating and removing the supernatant. This is preferable from the viewpoint of automation of measurement. After removing the supernatant, the solid phase capturing the complex may be washed with a suitable aqueous medium such as PBS.

Then, CDK4 contained in the complex on the solid phase is brought into contact with the substrate in the presence of adenosine triphosphate (ATP), thereby performing a phosphorylation reaction of the substrate by CDK4. This reaction can be performed by mixing and incubating the recovered solid phase with a buffer solution containing the substrate and ATP. The incubation time may be 2 minutes or more and 48 hours or less. The temperature condition may be 4° C. or more and 45° C. or less.

ATP may be labeled ATP or an ATP derivative. Examples of the labeled ATP include ATP labeled with a radioisotope, fluorescently labeled ATP, and the like. Examples of the ATP labeled with a radioisotope include ATP in which a phosphorus atom constituting ATP is substituted with an isotope (for example, $^{32}P$), and the like. Examples of the fluorescently labeled ATP include ATP to which a fluorescent substance such as a fluorescent dye is linked, and the like. Examples of the ATP derivative include ATP-γS (adenosine-5'-(γ-thio)-triphosphate) disclosed in JP 2002-335997 A, a DNP group-linked ATP derivative in which a dinitrophenyl (DNP) group is linked to the γ position of ATP disclosed in US 2015/0276740 A1, and the like.

The buffer solution is the same as that described for the buffer solution used for solubilizing cells or tissues. The buffer solution containing the substrate and ATP preferably further contains metal ions (for example, magnesium ions, manganese ions, or the like) necessary for exerting the activity of CDK.

After performing the phosphorylation reaction, the solid phase capturing the complex and the supernatant are separated, and only the supernatant is recovered. The means for separating the solid phase and the supernatant is not particularly limited, and may be the same as the B/F separation described above. The recovered supernatant contains a substrate phosphorylated by CDK4.

After recovering the supernatant, the amount of phosphorylated substrate in the supernatant is measured. The obtained measured value can be used as the measured value of CDK4 activity. The method for measuring the amount of the phosphorylated substrate is not particularly limited as long as quantitative measurement is possible. Such measuring methods are known per se, and examples thereof include enzyme-linked immunosorbent assay (ELISA), mass spectrometry, Western blot, and the like. In ELISA and Western blot, the amount of the phosphorylated substrate can be measured by specifically detecting the phosphorylated substrate. Since the phosphorylated substrate has an increased mass due to the addition of a phosphate group as compared to the original substrate, the amount of the phosphorylated substrate can be measured by detecting the phosphorylated substrate by mass spectrometry.

In the present embodiment, it is preferable to measure the amount of the phosphorylated substrate by ELISA. The ELISA may be any of a direct method, an indirect method, a sandwich method, and a competitive method. Hereinafter, a case where the amount of the phosphorylated substrate is measured by a direct method or indirect method using a detection substance that binds to a phosphorylated amino acid will be described as an example. In this example, using a supernatant obtained by a phosphorylation reaction using a biotin-tagged substrate and a solid phase on which avidins are immobilized, the substrate and the phosphorylated substrate are immobilized on the solid phase. However, the method of the present embodiment is not limited to this example. When the measurement is performed by the sandwich method, the substrate and the phosphorylated substrate can be immobilized on the solid phase, using a substance that binds to the substrate and the phosphorylated substrate.

First, a complex containing the phosphorylated substrate and the detection substance that binds to a phosphorylated amino acid is formed on the solid phase. The complex can be formed by mixing the recovered supernatant, the detection substance that binds to a phosphorylated amino acid, and the solid phase. The order of mixing is not particularly limited. Preferably, after mixing the phosphorylated substrate and the solid phase, the detection substance that binds to a phosphorylated amino acid is further mixed. In this example, the phosphorylated substrate is immobilized on the solid phase by binding of a biotin tag of the phosphorylated substrate and avidins on the solid phase. Then, the phosphorylated substrate immobilized on the solid phase and the detection substance that binds to a phosphorylated amino acid bind to form a complex on the solid phase.

The detection substance that binds to a phosphorylated amino acid may be any substance that specifically binds to the phosphorylated amino acid residue in the phosphorylated substrate. Examples of such substances include antibodies, aptamers, and the like. In a preferred embodiment, the detection substance that binds to a phosphorylated amino acid is an anti-phosphorylated amino acid antibody. Such antibodies include anti-phosphorylated serine/threonine antibodies, anti-phosphorylated serine antibodies, and anti-phosphorylated threonine antibodies. The anti-phosphorylated serine/threonine antibody is an antibody that specifically binds to both phosphorylated serine residues and phosphorylated threonine residues in protein or oligopeptide. Anti-phosphorylated amino acid antibodies are commercially available and generally available.

The solid phase used for measuring the amount of the phosphorylated substrate may be an insoluble carrier capable of immobilizing the phosphorylated substrate. The type and material of the solid phase are as described above. In a preferred embodiment, the solid phase is magnetic particles. In this example, a solid phase on which avidins are immobilized is used. However, when the substrate (including the phosphorylated substrate) has a tag other than a biotin tag, a capture substance that binds to the tag, for example, an antibody or aptamer that specifically binds to the tag may be immobilized on the solid phase. Alternatively, a capture substance that binds to the substrate (including the phosphorylated substrate) itself, for example, an antibody or aptamer that specifically binds to the substrate may be immobilized on the solid phase.

In the present embodiment, it is preferable that the detection substance that binds to a phosphorylated amino acid is labeled with a labeling substance. When the ELISA is a direct method, a detection substance to which a labeling substance is bound in advance is used in the step of forming the complex. When the ELISA is an indirect method, the solid phase on which the complex is formed is brought into contact with a substance (for example, a secondary antibody) that binds to the detection substance and has a labeling substance. Thereby, the phosphorylated substrate in the complex is labeled with the labeling substance via the detection substance. Then, by detecting a signal generated by the labeling substance, the amount of the phosphorylated substrate can be measured.

As used herein, the phrase "detecting a signal" includes qualitatively detecting the presence or absence of a signal, quantifying a signal intensity, and semi-quantitatively detecting the intensity of a signal. Semi-quantitative detection means to detect the intensity of the signal in stages such as "no signal generated", "weak", "medium", "strong", and the like. In the present embodiment, it is preferable to detect the intensity of a signal quantitatively or semi-quantitatively. In a more preferred embodiment, the intensity of the signal is detected quantitatively.

The labeling substance is not particularly limited. For example, the labeling substance may be a substance which itself generates a signal (hereinafter also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes. Examples of the enzymes include alkaline phosphatase, peroxidase, β-galactosidase, luciferase, and the like. Examples of the fluorescent substance include fluorescent dyes such as fluorescein isothiocyanate (FITC), rhodamine and Alexa Fluor (registered trademark), fluorescent proteins such as GFP, and the like. Examples of the radioactive isotopes include $^{125}I$, $^{14}C$, $^{32}P$, and the like. Among them, an enzyme is preferable as a labeling substance, and alkaline phosphatase and peroxidase are particularly preferable.

The substrate of the enzyme can be appropriately selected from known substrates according to the type of the enzyme. For example, when alkaline phosphatase is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.13,7]decan]-4-yl) phenyl phosphate) and CSPD (registered trademark) (disodium 3-(4-methoxyspiro[1,2-dioxetane-3,2-(5'-chloro)tricyclo[3.3.1.13,7]decan]-4-yl)phenyl phosphate), and chromogenic substrates such as 5-bromo-4-chloro-3-indolyl phosphate (BCIP), disodium 5-bromo-6-chloro-indolyl phosphate and p-nitrophenyl phosphate. When peroxidase is used as the enzyme, examples of the substrate include chemiluminescent substrates such as luminol and derivatives thereof, and chromogenic substrates such as 2,2'-azinobis(3-ethylbenzothiazoline-6-ammonium sulfonate) (ABTS), 1,2-phenylenediamine (OPD) and 3,3',5,5'-tetramethylbenzidine (TMB).

When the labeling substance is a radioactive isotope, radiation as a signal can be measured using a known apparatus such as a scintillation counter. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The detection result of the signal indicates the amount of the substrate phosphorylated by CDK4. As described above, a measured value indicating the amount of the phosphorylated substrate can be used as the measured value of CDK4 activity. For example, when quantitatively detecting the intensity of a signal, the signal intensity value itself or a value acquired from the measured value can be used as the measured value of CDK4 activity. Examples of the value acquired from the measured value of the signal intensity include a value acquired by subtracting the background value from the measured value, a value acquired by applying the measured value to a calibration curve, and the like.

In the present embodiment, each step or a series of steps of the phosphorylation reaction of the substrate by CDK and the measurement of the amount of the phosphorylated substrate may be performed by a hand method or by an apparatus. Examples of such apparatuses include automatic immunoassay apparatuses such as HISCL series (manufactured by Sysmex Corporation), and the like.

(Measurement of Expression Level of CDK)

In the present embodiment, a method for measuring the expression level of CDK is not particularly limited as long as a value reflecting the amount or concentration of CDK as protein in the sample can be acquired. Preferred sample is a liquid sample prepared from cells or tissues collected from a subject. The liquid sample used for measuring expression level is preferably the same as the liquid sample used for measuring the activity.

In a preferred embodiment, the method for measuring expression level is a method using a substance that specifically binds to CDK. The substance that specifically binds to CDK may be the same as the capture substance that binds to CDK used to measure the activity. The substance that specifically binds to CDK includes antibodies, aptamers, and the like. Preferably, the substance that specifically binds to CDK4 is an anti-CDK4 antibody, and the substance that specifically binds to CDK6 is an anti-CDK6 antibody. Methods for measuring expression level using an antibody are known, and examples thereof include Western blot, ELISA, and the like. In any measuring method, it is preferable to measure a predetermined amount or concentration of each CDK recombinant protein as a reference sample for quantitative measurement. A calibration curve or the like may be created from the measured values of the reference sample.

In the present embodiment, it is preferable to measure the expression level of each CDK in a liquid sample prepared from cells or tissues collected from a subject. Hereinafter, measurement of the expression level of CDK in a liquid sample by Western blot will be described.

First, the total protein concentration of the liquid sample is measured. Methods for measuring total protein concentration are known, and examples thereof include BCA method, Bradford method, Lowry method, and the like. A commercially available kit for measuring total protein concentration may be used. After the measurement of total protein concentration, the liquid sample may be diluted as necessary to adjust the liquid sample to a predetermined total protein concentration. Then, a sample for electrophoresis is prepared from a predetermined amount of a liquid sample with a known concentration. The obtained sample for electrophoresis is electrophoresed on a suitable gel such as polyacrylamide gel. At this time, a predetermined amount of recombinant CDK4 or CDK6 with a known concentration is also electrophoresed. After the electrophoresis, the proteins in the gel are transferred to a suitable membrane such as a PVDF membrane, and a primary reaction is performed using an anti-CDK4 antibody or an anti-CDK6 antibody. Then, a secondary reaction is performed using an antibody labeled with a labeling substance, and a signal generated by the labeling substance is detected, whereby CDK4 or CDK6 on the membrane is measured.

The labeling substance is not particularly limited, but is preferably an enzyme such as peroxidase. The substrate for the enzyme is as described above. In the present embodiment, it is preferable to acquire an image of the membrane using a device capable of detecting a signal by the labeling substance, for example, a CCD imager, densitometry, or the like. The detection results are quantitatively analyzed by known image analysis software such as Image Lab (Bio-Rad) to acquire a measured value of expression level of CDK4 or CDK6.

(Comparison with Threshold Level and Determination)

When a value based on CDK activity of any one of CDK4 and CDK6 is used, determination can be made as follows. In one embodiment, when using a value based on CDK4 activity, the value based on the CDK4 activity is compared with a threshold level corresponding to CDK4. When the value based on the CDK4 activity is less than the threshold level, the subject may be determined to be insensitive to a CDK4/6 inhibitor. When the value based on the CDK4 activity is greater than or equal to the threshold level, the subject may be determined to be sensitive to the CDK4/6 inhibitor.

In another embodiment, when using a value based on CDK6 activity, the value based on the CDK6 activity is compared with a threshold level corresponding to CDK6. When the value based on the CDK6 activity is less than the threshold level, the subject may be determined to be insensitive to the CDK4/6 inhibitor. When the value based on the CDK6 activity is greater than or equal to the threshold level, the subject may be determined to be sensitive to the CDK4/6 inhibitor.

In another embodiment, when both the value based on the CDK4 activity and the value based on the CDK6 activity are used, determination can be made as follows. The value based on the CDK4 activity is compared with a first threshold level, and the value based on the CDK6 activity is compared with a second threshold level. In this example, the first threshold level is the threshold level corresponding to CDK4, and the second threshold level is the threshold level corresponding to CDK6. When the value based on the CDK4 activity is less than the first threshold level or the value based on the CDK6 activity is less than the second threshold level, the subject may be determined to be insensitive to the CDK4/6 inhibitor. When the value based on the CDK4 activity is greater than or equal to the first threshold level and the value based on the CDK6 activity is greater than or equal to the second threshold level, the subject may be determined to be sensitive to the CDK4/6 inhibitor.

In yet another embodiment, the value based on the CDK4 activity is compared with the first threshold level, and the value based on the CDK6 activity is compared with a second threshold level. In this example, the first threshold level is the threshold level corresponding to CDK4, and the second threshold level is the threshold level corresponding to CDK6. When the value based on the CDK4 activity is less than the first threshold level and the value based on the CDK6 activity is less than the second threshold level, the subject may be determined to be insensitive to the CDK4/6 inhibitor. When the value based on the CDK4 activity is greater than or equal to the first threshold level and the value based on the CDK6 activity is greater than or equal to the second threshold level, the subject may be determined to be sensitive to the CDK4/6 inhibitor. When the value based on the CDK4 activity is less than the first threshold level and the value based on the CDK6 activity is greater than or equal to the second threshold level, or the value based on the CDK4 activity is greater than or equal to the first threshold level, and the value based on the CDK6 activity is less than the second threshold level, the subject may be determined to have a moderate sensitivity to the CDK4/6 inhibitor. Alternatively, the necessity of administration of the CDK4/6 inhibitor may be determined based on other medical findings without showing the determination result of the sensitivity.

As used herein, the phrase "the subject is sensitive to the CDK4/6 inhibitor" means that "there is a high possibility that the CDK4/6 inhibitor responds to the subject", and can be rephrased as "the subject is selected as an administration target of the CDK4/6 inhibitor." As used herein, the phrase "the subject is insensitive to the CDK4/6 inhibitor" means that "there is a low possibility that the CDK4/6 inhibitor responds to the subject", and can be rephrased as "the subject is not selected as an administration target of the CDK4/6 inhibitor." As used herein, the phrase "the subject has a moderate sensitivity to the CDK4/6 inhibitor" means that "there is a moderate possibility that the CDK4/6 inhibitor responds to the subject", and can be rephrased as "the subject may be selected as an administration target of the CDK4/6 inhibitor."

The threshold level corresponding to each CDK can be set as appropriate. The threshold level can be set, for example, from a value based on CDK activity in a sample collected from a cancer patient who is sensitive to the CDK4/6 inhibitor and a cancer patient who is insensitive to the CDK4/6 inhibitor. For example, the predetermined threshold level may be set as follows. First, samples are collected from a plurality of cancer patients, and a value based on activity of each CDK is acquired. After collecting the samples, a CDK4/6 inhibitor is administered to the cancer patient, and the process is observed. Sensitivity of each cancer patient to a CDK4/6 inhibitor is confirmed based on known diagnostic methods such as changes in tumor size, cytodiagnosis, and histological diagnosis. Then, the cancer patients are classified into a group sensitive to the CDK4/6 inhibitor and a group insensitive to the CDK4/6 inhibitor. From the values based on the CDK activities for the patients in each group, a value that can distinguish between the group sensitive to the CDK4/6 inhibitor and the group insensitive to the CDK4/6 inhibitor is determined, and the value is set as a predetermined threshold level. In setting the threshold level, it is preferable to also consider the sensitivity, specificity, positive predictive value, and negative predictive value of the determination.

(Value Based on CDK2 Activity)

The present inventors have found that values based on CDK2 activities also differ between cancer cell lines with different sensitivities to the CDK4/6 inhibitor. Therefore, in the determination method of the present embodiment, it is preferable to acquire a value based on activity of at least one CDK selected from CDK4 and CDK6 and the value based on the CDK2 activity.

The value based on the CDK2 activity is a value acquired using a measured value of the CDK2 activity and a measured value of expression level of CDK2. The CDK2 activity can be measured in the same manner as the CDK4 and CDK6 activities by using a capture substance that binds to CDK2 and a substrate for CDK2. The expression level of CDK2 can be measured in the same manner as the expression levels of CDK4 and CDK6 by using a substance that specifically binds to CDK2. The capture substance that binds to CDK2 and the substance that specifically binds to CDK2 include antibodies, aptamers, and the like. In the present embodiment, it is preferable to use an anti-CDK2 antibody. The substrate for CDK2 is similar to the substrates for CDK4 and CDK6.

In a preferred embodiment, the value based on the CDK2 activity is a specific activity value of CDK2. The specific activity value of CDK2 can be calculated by the following equation. Alternatively, a value (for example, a product, ratio, sum, difference, or the like) acquired using a value calculated by the following equation and a predetermined constant or coefficient may be used as the specific activity value of CDK2.

[Specific activity value of CDK2]=[Measured value of CDK2 activity]/[Measured value of expression level of CDK2]

In a more preferred embodiment, the value based on the CDK2 activity is a ratio of the specific activity value of CDK2 in a sample treated with a CDK4/6 inhibitor to the specific activity value of CDK2 in a sample not treated with a CDK4/6 inhibitor. The ratio value of the specific activity of CDK2 can be calculated by the following equation. Alternatively, a value (for example, a product, ratio, sum, difference, or the like) acquired using a value calculated by the following equation and a predetermined constant or coefficient may be used as the ratio value of the specific activity of CDK2.

[Ratio value of specific activity of CDK2]=[Specific activity value of CDK2 of sample treated with CDK4/6 inhibitor]/[Specific activity value of CDK2 of sample not treated with CDK4/6 inhibitor]

In the determination method of the present embodiment, it is preferable to compare the value based on the activity of at least one CDK selected from CDK4 and CDK6, with a threshold level corresponding to the CDK, compare the value based on the CDK2 activity, with a threshold level corresponding to CDK2, and determine sensitivity of the subject to a CDK4/6 inhibitor based on the comparison result. Details of the threshold level and determination result corresponding to each CDK are as described above.

In one embodiment, when the value based on the CDK4 activity and the value based on the CDK2 activity are used, determination can be made as follows. The value based on the CDK4 activity is compared with a first threshold level, and the value based on the CDK2 activity is compared with a second threshold level. In this example, the first threshold level is the threshold level corresponding to CDK4, and the second threshold level is the threshold level corresponding to CDK2. When the value based on the CDK4 activity is less than the first threshold level and the value based on the CDK2 activity is greater than or equal to the second threshold level, the subject may be determined to be insensitive to the CDK4/6 inhibitor. When the value based on the CDK4 activity is greater than or equal to the first threshold level and the value based on the CDK2 activity is less than the second threshold level, the subject may be determined to be sensitive to the CDK4/6 inhibitor.

On the other hand, when the value based on the CDK4 activity is less than the first threshold level, and the value based on the CDK2 activity is less than the second threshold level, or the value based on the CDK4 activity is greater than or equal to the first threshold level, and the value based on the CDK2 activity is greater than or equal to the second threshold level, the subject may be determined to have a moderate sensitivity to the CDK4/6 inhibitor. Alternatively, the necessity of administration of the CDK4/6 inhibitor may be determined based on other medical findings without showing the determination result of the sensitivity.

In another embodiment, when the value based on the CDK6 activity and the value based on the CDK2 activity are used, determination can be made as follows. The value based on the CDK6 activity is compared with the first threshold level, and the value based on the CDK2 activity is compared with the second threshold level. In this example, the first threshold level is the threshold level corresponding to CDK6, and the second threshold level is the threshold level corresponding to CDK2. When the value based on the CDK6 activity is less than the first threshold level and the value based on the CDK2 activity is greater than or equal to the second threshold level, the subject may be determined to be insensitive to the CDK4/6 inhibitor. When the value based on the CDK6 activity is greater than or equal to the first threshold level and the value based on the CDK2 activity is less than the second threshold level, the subject may be determined to be sensitive to the CDK4/6 inhibitor.

On the other hand, when the value based on the CDK6 activity is less than the first threshold level, and the value based on the CDK2 activity is less than the second threshold level, or the value based on the CDK6 activity is greater than or equal to the first threshold level, and the value based on the CDK2 activity is greater than or equal to the second threshold level, the subject may be determined to have a moderate sensitivity to the CDK4/6 inhibitor. Alternatively, the necessity of administration of the CDK4/6 inhibitor may be determined based on other medical findings without showing the determination result of the sensitivity.

In another embodiment, when the value based on the CDK4 activity, the value based on the CDK6 activity and the value based on the CDK2 activity are used, determination can be made as follows. The value based on the CDK4 activity is compared with a first threshold level, the value based on the CDK6 activity is compared with a second threshold level, and the value based on the CDK2 activity is compared with a third threshold level. In this example, the first threshold level is the threshold level corresponding to CDK4, the second threshold level is the threshold level corresponding to CDK6, and the third threshold level is the threshold level corresponding to CDK2. When the value based on the CDK4 activity is less than the first threshold level, the value based on the CDK6 activity is less than the second threshold level, and the value based on the CDK2 activity is greater than or equal to the third threshold level, the subject may be determined to be insensitive to the CDK4/6 inhibitor. When the value based on the CDK4 activity is greater than or equal to the first threshold level, the value based on the CDK6 activity is greater than or equal to the second threshold level, and the value based on the CDK2 activity is less than the third threshold level, the subject may be determined to be sensitive to the CDK4/6 inhibitor.

On the other hand, the subject may be determined to have a moderate sensitivity to the CDK4/6 inhibitor in the following cases. Alternatively, the necessity of administration of the CDK4/6 inhibitor may be determined based on other medical findings without showing the determination result of the sensitivity.

When the value based on the CDK4 activity is less than the first threshold level, the value based on the CDK6 activity is less than the second threshold level, and the value based on the CDK2 activity is less than the third threshold level;

when the value based on the CDK4 activity is greater than or equal to the first threshold level, the value based on the CDK6 activity is greater than or equal to the second threshold level, and the value based on the CDK2 activity is greater than or equal to the third threshold level;

when the value based on the CDK4 activity is less than the first threshold level, the value based on the CDK6 activity is greater than or equal to the second threshold level, and the value based on the CDK2 activity is less than the third threshold level;

when the value based on the CDK4 activity is greater than or equal to the first threshold level, the value based on the CDK6 activity is less than the second threshold level, and the value based on the CDK2 activity is less than the third threshold level;

when the value based on the CDK4 activity is less than the first threshold level, the value based on the CDK6 activity is greater than or equal to the second threshold level, and the value based on the CDK2 activity is greater than or equal to the third threshold level; or when the value based on the CDK4 activity is greater than or equal to the first threshold level, the value based on the CDK6 activity is less than the second threshold level, and the value based on the CDK2 activity is greater than or equal to the third threshold level.

When the subject has not yet received treatment with a CDK4/6 inhibitor, the determination method of the present embodiment enables to determine whether the subject is sensitive to the CDK4/6 inhibitor before administration of the CDK4/6 inhibitor. When the subject has received treatment with a CDK4/6 inhibitor, the determination method of the present embodiment enables to determine whether the subject has developed resistance to the CDK4/6 inhibitor. As described above, the determination method of the present embodiment can provide doctors and the like with information to assist determination of sensitivity to the CDK4/6 inhibitor. Such information is useful for considering starting, continuing or stopping treatment with a CDK4/6 inhibitor. The determination method of the present embodiment can be rephrased as a method for determining the efficacy of a CDK4/6 inhibitor or a method for predicting the effect of a CDK4/6 inhibitor.

(Modified Example of Determination Method of Present Embodiment)

In a further embodiment, samples collected from a subject are divided to acquire first and second aliquots, and the specific activity value of CDK in each aliquot may be used to determine sensitivity to the CDK4/6 inhibitor. In this modified example, the first aliquot is preferably an aliquot not treated with a CDK4/6 inhibitor, and the second aliquot is preferably an aliquot treated in vitro with a CDK4/6 inhibitor. According to this example, sensitivity of the subject to the CDK4/6 inhibitor can be determined from a sample obtained by one collection. Specifically, by using the specific activity value of CDK in each aliquot obtained by dividing the samples, sensitivity to the CDK4/6 inhibitor can be determined based on change in the specific activity of CDK between before and after addition of the CDK4/6 inhibitor.

As the first aliquot, cells or tissues not treated with a CDK4/6 inhibitor are preferred. For example, one aliquot obtained by dividing cells or tissues collected from a subject into two can be used as it is as a first aliquot. More preferably, the first aliquot is a liquid sample prepared from cells or tissues that have not been treated with a CDK4/6 inhibitor.

As the second aliquot, cells or tissues treated in vitro with a CDK4/6 inhibitor are preferred. Such a second aliquot can be obtained by adding a CDK4/6 inhibitor to the other aliquot obtained by dividing cells or tissues collected from a subject into two and incubating for a predetermined time. More preferably, the second aliquot is a liquid sample prepared from cells or tissues treated in vitro with a CDK4/6 inhibitor. The incubation time and final concentration of CDK4/6 inhibitor are as described above.

In this example, a value of specific activity of the first CDK in the first aliquot (also referred to as "first specific activity") and a value of specific activity of the first CDK in the second aliquot (also referred to as "second specific activity") are acquired. The first CDK is CDK4 or CDK6. The first specific activity value and the second specific activity value can be acquired in the same manner as the specific activity value of each CDK described in the determination method of the present embodiment.

In this example, a ratio value of the first specific activity value and the second specific activity value is used to determine sensitivity to the CDK4/6 inhibitor. Examples of such ratios include a ratio of the second specific activity value to the first specific activity value ([Second specific activity value]/[First specific activity value]), or a ratio of the first specific activity value to the second specific activity value ([First specific activity value]/[Second specific activity value]). Alternatively, a value (for example, a product, ratio, sum, difference, or the like) acquired using these ratio values and a predetermined constant or coefficient may be used.

In this example, when the ratio value of the second specific activity value to the first specific activity value is less than a predetermined threshold level, or the ratio value of the first specific activity value to the second specific activity value is greater than or equal to the predetermined threshold level, the subject is determined to be insensitive to the CDK4/6 inhibitor. When the ratio value of the second specific activity value to the first specific activity value is greater than or equal to the predetermined threshold level, or the ratio value of the first specific activity value to the second specific activity value is less than the predetermined threshold level, the subject is determined to be sensitive to the CDK4/6 inhibitor. The predetermined threshold level can be appropriately determined in the same manner as the threshold level corresponding to the CDK.

In the modified example, determination may be made using specific activity values of a plurality of CDKs in the first and second aliquots. Hereinafter, a case where specific activity values of two CDKs of CDK4 or CDK6 and CDK2 are used will be described as an example. First, in the step of acquiring specific activity values, in addition to the values of the first specific activity and the second specific activity, a value of specific activity of the second CDK in the first aliquot (also referred to as "third specific activity") and a value of specific activity of the second CDK in the second aliquot (also referred to as "fourth specific activity") are further acquired. In this case, the first CDK is CDK4 or CDK6, and the second CDK is CDK2. The third specific activity value and the fourth specific activity value can be acquired in the same manner as the specific activity value of each CDK described in the determination method of the present embodiment.

Next, a ratio value of the first specific activity value and the second specific activity value and a ratio value of the third specific activity value and the fourth specific activity value are acquired. Examples of the ratio of the third specific activity value and the fourth specific activity value include a ratio value of the fourth specific activity value to the third specific activity value ([Fourth specific activity value]/[Third specific activity value]), or a ratio value of the third specific activity value to the fourth specific activity value ([Third specific activity value]/[Fourth specific activity value]). Alternatively, a value (for example, a product, ratio, sum, difference, or the like) acquired using these ratio values and a predetermined constant or coefficient may be used.

A subject is determined to be insensitive to the CDK4/6 inhibitor in the following cases. The first and second threshold levels can be appropriately determined in the same manner as the threshold level corresponding to the CDK.

When the ratio value of the second specific activity value to the first specific activity value is less than the first threshold level, and the ratio value of the fourth specific activity value to the third specific activity value is greater than or equal to the second threshold level; or when the ratio value of the first specific activity value to the second specific activity value is greater than or equal to the first threshold level, and the ratio value of the third specific activity value to the fourth specific activity value is less than the second threshold level.

A subject is determined to be sensitive to the CDK4/6 inhibitor in the following cases.

When the ratio value of the second specific activity value to the first specific activity value is greater than or equal to the first threshold level, and the ratio value of the fourth specific activity value to the third specific activity value is less than the second threshold level; or when the ratio value of the first specific activity value to the second specific activity value is less than the first threshold level, and the ratio value of the third specific activity value to the fourth specific activity value is greater than or equal to the second threshold level.

A case where specific activity values of three CDKs of CDK4, CDK6 and CDK2 are used will be described as an example. First, in the step of acquiring specific activity values, in addition to the values of the first specific activity and the second specific activity, the third specific activity value, and the fourth specific activity value, a value of specific activity of the third CDK in the first aliquot (also referred to as "fifth specific activity") and a value of specific activity of the third CDK in the second aliquot (also referred to as "sixth specific activity") are further acquired. In this example, the first CDK is CDK4, the second CDK is CDK6, and the third CDK is CDK2. The fifth specific activity value and the sixth specific activity value can be acquired in the same manner as the specific activity value of each CDK described in the determination method of the present embodiment.

Next, a ratio value of the first specific activity value and the second specific activity value, a ratio value of the third specific activity value and the fourth specific activity value and a ratio value of the fifth specific activity value and the sixth specific activity value are acquired. Examples of the ratio of the fifth specific activity value and the sixth specific activity value include a ratio value of the sixth specific activity value to the fifth specific activity value ([Sixth specific activity value]/[Fifth specific activity value]), or a ratio value of the fifth specific activity value to the sixth specific activity value ([Fifth specific activity value]/[Sixth specific activity value]). Alternatively, a value (for example, a product, ratio, sum, difference, or the like) acquired using these ratio values and a predetermined constant or coefficient may be used.

A subject is determined to be insensitive to the CDK4/6 inhibitor in the following cases. The first, second and third threshold levels can be appropriately determined in the same manner as the threshold level corresponding to the CDK.

When the ratio value of the second specific activity value to the first specific activity value is less than the first threshold level, the ratio value of the fourth specific activity value to the third specific activity value is less than the second threshold level, and the ratio value of the sixth specific activity value to the fifth specific activity value is greater than or equal to the third threshold level; or when the ratio value of the first specific activity value to the second specific activity value is greater than or equal to the first threshold level, the ratio value of the third specific activity value to the fourth specific activity value is greater than or equal to the second threshold level, and the ratio value of the fifth specific activity value to the sixth specific activity value is less than the third threshold level.

A subject is determined to be sensitive to the CDK4/6 inhibitor in the following cases.

When the ratio value of the second specific activity value to the first specific activity value is greater than or equal to the first threshold level, the ratio value of the fourth specific activity value to the third specific activity value is greater than or equal to the second threshold level, and the ratio value of the sixth specific activity value to the fifth specific activity value is less than the third threshold level; or when the ratio value of the first specific activity value to the second specific activity value is less than the first threshold level, the ratio value of the third specific activity value to the fourth specific activity value is less than the second threshold level, and the ratio value of the fifth specific activity value to the sixth specific activity value is greater than or equal to the third threshold level.

[2. Method for Determining Sensitivity to CDK4/6 Inhibitor of Subject Who has been Administered CDK4/6 Inhibitor]

One embodiment relates to a method for determining sensitivity to a CDK4/6 inhibitor of a subject who has been administered a CDK4/6 inhibitor. As described above, in the treatment with a CDK4/6 inhibitor, acquisition of resistance is a problem. According to the determination method of the present embodiment, since sensitivity to the CDK4/6 inhibitor can be determined based on the specific activity value of CDK in a sample collected from the subject, it is possible to monitor whether the subject has developed resistance to the CDK4/6 inhibitor based on change in the specific activity of CDK between before and after administration of the inhibitor. According to this determination method, it is possible to provide doctors and the like with information to assist in determining whether or not to continue treatment with a CDK4/6 inhibitor. Details of the subject, CDK4/6 inhibitor, sample, acquisition of specific activity of CDK and the like are the same as those described for the above determination method.

In the present embodiment, a sample collected from the subject before administration of the CDK4/6 inhibitor (also referred to as "first sample") and a sample collected from the subject after administration of the CDK4/6 inhibitor (also referred to as "second sample") are used. As the first sample and the second sample, cells or tissues collected from the subject are preferable, and a liquid sample prepared from cells or tissues are more preferable. Collection timing of the first sample is not particularly limited as long as it is before administration of the CDK4/6 inhibitor to the subject. Collection timing of the second sample is not particularly limited as long as it is after administration of the CDK4/6 inhibitor to the subject, and is 1 day to 16 weeks after administration, and preferably 2 days to 12 weeks and more preferably after 4 weeks to 12 weeks after administration. Generally, when the subject is a cancer patient, the subject needs to visit a hospital for follow-up for a while after the start of treatment, thus a sample may be collected at the time of this visit.

In the present embodiment, a value of specific activity of the first CDK in the first sample (also referred to as "first specific activity") and a value of specific activity of the first CDK in the second sample (also referred to as "second specific activity") are acquired. The first CDK is CDK4 or CDK6. The values of the first specific activity and the second specific activity can be acquired in the same manner as the specific activity value of each CDK described in the determination method of the present embodiment.

In the present embodiment, the ratio value of the first specific activity value and the second specific activity value is used to determine sensitivity to the CDK4/6 inhibitor of the subject who has been administered the CDK4/6 inhibitor. Examples of such ratios include a ratio of the second specific activity value to the first specific activity value ([Second specific activity value]/[First specific activity value]), or a ratio of the first specific activity value to the second specific activity value ([First specific activity value]/[Second specific activity value]). Alternatively, a value (for example, a product, ratio, sum, difference, or the like) acquired using these ratio values and a predetermined constant or coefficient may be used.

In the present embodiment, when the ratio value of the second specific activity value to the first specific activity value is less than a predetermined threshold level, or the ratio value of the first specific activity value to the second specific activity value is greater than or equal to the predetermined threshold level, the subject is determined to be insensitive to the CDK4/6 inhibitor. When the subject is determined to be insensitive, it may be determined that the subject has developed resistance to the CDK4/6 inhibitor When the ratio value of the second specific activity value to the first specific activity value is greater than or equal to the predetermined threshold level, or the ratio value of the first specific activity value to the second specific activity value is less than the predetermined threshold level, the subject is determined to be sensitive to the CDK4/6 inhibitor. When the subject is determined to be sensitive, it may be determined that the subject has not developed resistance to the CDK4/6 inhibitor. The predetermined threshold level can be appropriately determined in the same manner as the threshold level corresponding to the CDK.

In the present embodiment, determination may be made using specific activity values of a plurality of CDKs in the first sample and the second sample. Hereinafter, a case where specific activity values of two CDKs of CDK4 or CDK6 and CDK2 are used will be described as an example. First, in the step of acquiring specific activity values, in addition to the values of the first specific activity and the second specific activity, a value of specific activity of the second CDK in the first sample (also referred to as "third specific activity") and a value of specific activity of the second CDK in the second sample (also referred to as "fourth specific activity") are further acquired. In this case, the first CDK is CDK4 or CDK6, and the second CDK is CDK2. The third specific activity value and the fourth specific activity value can be acquired in the same manner as the specific activity value of each CDK described in the determination method of the present embodiment.

Next, a ratio value of the first specific activity value and the second specific activity value and a ratio value of the third specific activity value and the fourth specific activity value are acquired. Examples of the ratio of the third specific activity value and the fourth specific activity value include a ratio value of the fourth specific activity value to the third specific activity value ([Fourth specific activity value]/[Third specific activity value]), or a ratio value of the third specific activity value to the fourth specific activity value ([Third specific activity value]/[Fourth specific activity value]). Alternatively, a value (for example, a product, ratio, sum, difference, or the like) acquired using these ratio values and a predetermined constant or coefficient may be used.

In the following cases, a subject who has been administered a CDK4/6 inhibitor is determined to be insensitive to the CDK4/6 inhibitor. The first and second threshold levels can be appropriately determined in the same manner as the threshold level corresponding to the CDK.

When the ratio value of the second specific activity value to the first specific activity value is less than the first threshold level, and the ratio value of the fourth specific activity value to the third specific activity value is greater than or equal to the second threshold level; or when the ratio value of the first specific activity value to the second specific activity value is greater than or equal to the first threshold level, and the ratio value of the third specific activity value to the fourth specific activity value is less than the second threshold level.

In the following cases, a subject who has been administered a CDK4/6 inhibitor is determined to be sensitive to the CDK4/6 inhibitor.

When the ratio value of the second specific activity value to the first specific activity value is greater than or equal to the first threshold level, and the ratio value of the fourth specific activity value to the third specific activity value is less than the second threshold level; or when the ratio value of the first specific activity value to the second specific activity value is less than the first threshold level, and the ratio value of the third specific activity value to the fourth specific activity value is greater than or equal to the second threshold level.

A case where specific activity values of three CDKs of CDK4, CDK6 and CDK2 are used will be described as an example. First, in the step of acquiring specific activity values, in addition to the values of the first specific activity and the second specific activity, the third specific activity value, and the fourth specific activity value, a value of specific activity of the third CDK in the first sample (also referred to as "fifth specific activity") and a value of specific activity of the third CDK in the second sample (also referred to as "sixth specific activity") are further acquired. In this example, the first CDK is CDK4, the second CDK is CDK6, and the third CDK is CDK2. The fifth specific activity value and the sixth specific activity value can be acquired in the same manner as the specific activity value of each CDK described in the determination method of the present embodiment.

Next, a ratio value of the first specific activity value and the second specific activity value, a ratio value of the third specific activity value and the fourth specific activity value and a ratio value of the fifth specific activity value and the sixth specific activity value are acquired. Examples of the ratio of the fifth specific activity value and the sixth specific activity value include a ratio value of the sixth specific activity value to the fifth specific activity value ([Sixth specific activity value]/[Fifth specific activity value]), or a ratio value of the fifth specific activity value to the sixth specific activity value ([Fifth specific activity value]/[Sixth specific activity value]). Alternatively, a value (for example, a product, ratio, sum, difference, or the like) acquired using these ratio values and a predetermined constant or coefficient may be used.

In the following cases, a subject who has been administered a CDK4/6 inhibitor is determined to be insensitive to the CDK4/6 inhibitor. The first, second and third threshold levels can be appropriately determined in the same manner as the threshold level corresponding to the CDK.

When the ratio value of the second specific activity value to the first specific activity value is less than the first threshold level, the ratio value of the fourth specific activity value to the third specific activity value is less than the second threshold level, and the ratio value of the sixth specific activity value to the fifth specific activity value is greater than or equal to the third threshold level; or when the ratio value of the first specific activity value to the second specific activity value is greater than or equal to the first threshold level, the ratio value of the third specific activity value to the fourth specific activity value is greater than or equal to the second threshold level, and the ratio value of the fifth specific activity value to the sixth specific activity value is less than the third threshold level.

In the following cases, a subject who has been administered a CDK4/6 inhibitor is determined to be sensitive to the CDK4/6 inhibitor.

When the ratio value of the second specific activity value to the first specific activity value is greater than or equal to the first threshold level, the ratio value of the fourth specific activity value to the third specific activity value is greater than or equal to the second threshold level, and the ratio value of the sixth specific activity value to the fifth specific activity value is less than the third threshold level; or when the ratio value of the first specific activity value to the second specific activity value is less than the first threshold level, the ratio value of the third specific activity value to the fourth specific activity value is less than the second threshold level, and the ratio value of the fifth specific activity value to the sixth specific activity value is greater than or equal to the third threshold level.

[3. Method for Treating Cancer]

One embodiment relates to a method for treating cancer. The method for treating cancer of the present embodiment includes the steps of comparing a value based on activity of at least one CDK selected from CDK4 and CDK6 in a sample collected from a cancer patient, with a threshold level corresponding to the CDK, determining that the subject is sensitive to a CDK4/6 inhibitor when the value based on the CDK activity is greater than or equal to the threshold level, and administering a CDK4/6 inhibitor to a patient determined to be sensitive to the CDK4/6 inhibitor.

In the present embodiment, it is preferable to further use a value based on CDK2 activity. That is, the method for treating cancer of the present embodiment preferably includes the steps of comparing a value based on activity of at least one CDK selected from CDK4 and CDK6, with a threshold level corresponding to the CDK, comparing a value based on the CDK2 activity, with a threshold level corresponding to CDK2, and administering a CDK4/6 inhibitor to the subject when the subject is determined to be sensitive to the CDK4/6 inhibitor, based on the comparison result.

Details of the type of cancer, CDK4/6 inhibitor, sample, value based on the CDK activity, threshold level, comparison step, determination step and the like are the same as those described for the above determination method. The treatment method of the present embodiment is particularly suitable for breast cancer patients. In the administration step, it is preferable to administer a therapeutically effective amount of a CDK4/6 inhibitor to a cancer patient. The therapeutically effective amount is appropriately determined according to the type of cancer, the degree of progression of cancer, the type of CDK4/6 inhibitor, treatment guidelines, and the like.

[4. Method for Acquiring Value Based on CDK Activity]

The value based on the CDK activity obtained by the above determination method can also be said to be information suggesting sensitivity of the subject to the CDK4/6 inhibitor. Therefore, the scope of the present disclosure also includes a method for acquiring a value based on CDK activity (hereinafter, also referred to as "acquisition method"). The acquisition method of the present embodiment includes the step of acquiring a value based on activity of at least one CDK selected from CDK4 and CDK6 in a sample collected from a subject, and when the acquired value based on the CDK activity is less than a threshold level corresponding to the CDK, it is suggested that the subject is insensitive to the CDK4/6 inhibitor.

In the acquisition method of the present embodiment, first, a value based on activity of at least one CDK selected from CDK4 and CDK6 in a sample collected from a subject is acquired. Details of the subject, CDK4/6 inhibitor, sample and value based on the CDK activity are the same as those described for the above determination method. In a preferred embodiment, the subject is a cancer patient, especially, a breast cancer patient. The subject may be a cancer patient (especially, a breast cancer patient) who has undergone treatment with a CDK4/6 inhibitor.

The value based on the CDK activity obtained by the acquisition method of the present embodiment is information suggesting sensitivity of the subject to the CDK4/6 inhibitor, by comparison with the threshold level corresponding to each CDK. For example, when the acquired value based on the CDK activity is less than the threshold level corresponding to the CDK, it is suggested that the subject is insensitive to the CDK4/6 inhibitor. When the acquired value based on the CDK activity is greater than or equal to the threshold level corresponding to the CDK, it is suggested that the subject is sensitive to the CDK4/6 inhibitor.

In the present embodiment, it is preferable to further acquire a value based on CDK2 activity. That is, in the acquisition method of the present embodiment, the value based on the activity of at least one CDK selected from CDK4 and CDK6 is less than the threshold level corresponding to the CDK, and the value based on the CDK2 activity is greater than or equal to the threshold level corresponding to CDK2, it is suggested that the subject is insensitive to the CDK4/6 inhibitor. That is, in the acquisition method of the present embodiment, the value based on the activity of at least one CDK selected from CDK4 and CDK6 is greater than or equal to the threshold level corresponding to the CDK, and the value based on the CDK2 activity is less than the threshold level corresponding to CDK2, it is suggested that the subject is sensitive to the CDK4/6 inhibitor.

[5. Reagent Kit]

The scope of the present disclosure also includes a reagent kit for use in the above determination method or acquisition method. The reagent kit of the present embodiment contains a capture substance that binds to at least one CDK selected from CDK4 and CDK6, and a substrate for the CDK. The reagent kit preferably contains a capture substance that binds to CDK4, a capture substance that binds to CDK6, and substrates for CDK4 and CDK6. In this embodiment, the substrates for CDK4 and CDK6 may be a common substrate for CDK4 and CDK6. Alternatively, the substrates for CDK4 and CDK6 may be a combination of a substrate for CDK4 and a substrate for CDK6.

In a further embodiment, the reagent kit may further contain a capture substance that binds to CDK2 and a substrate for CDK2. The substrate for CDK2 may be a common substrate for CDK2, CDK4 and CDK6. In this case, the reagent kit contains a capture substance that binds to CDK4, a capture substance that binds to CDK6, a capture substance that binds to CDK2, and substrates for CDK2, CDK4, and CDK6.

Details of the capture substance that binds to CDK and substrate for CDK are the same as those described for the above determination method. In the present embodiment, an antibody is particularly preferable as the capture substance that binds to CDK. As the substrate for CDK, a substrate peptide described in EP 3 404 038 A1 is preferable.

The reagent kit of the present embodiment may further contain a solid phase for immobilizing the capture substance that binds to CDK. The reagent kit of the present embodiment may further contain a buffer solution containing ATP. Details of the solid phase, ATP and buffer solution are the same as those described for the above determination method.

The reagent kit of the present embodiment may further contain a solid phase for immobilizing the substrate and a phosphorylated substrate. The reagent kit of the present embodiment may further contain a detection substance that binds to a phosphorylated amino acid. Details of the solid phase and detection substance that binds to a phosphorylated amino acid are the same as those described for the above determination method.

The reagent kit of the present embodiment may further contain a substance that specifically binds to CDK for measuring expression level of CDK. Details of the substance that specifically binds to CDK are the same as those described for the above determination method. In the present embodiment, an antibody is particularly preferable as the substance that specifically binds to CDK.

FIG. 1A shows an example of the reagent kit of the present embodiment. In FIG. 1A, 11 denotes a reagent kit, 12 denotes a first container containing a reagent containing a capture substance that binds to CDK4 or CDK6, 13 denotes a second container containing a reagent containing a substrate, 14 denotes a packing box, and 15 denotes an attached document. In this example, the substrate is a common substrate for CDK4 and CDK6.

Figure 1B:
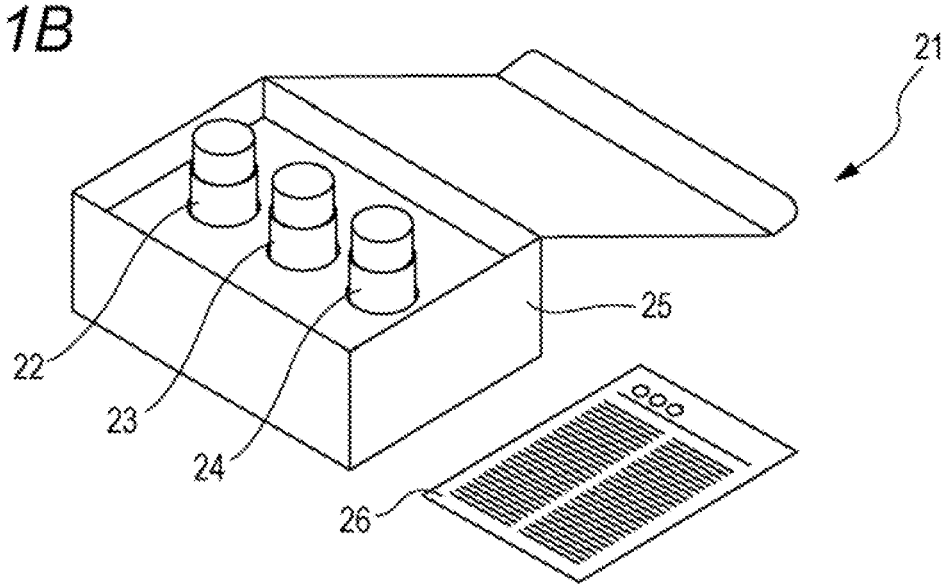
FIG. 1B is a schematic diagram showing an example of the reagent kit of the present embodiment.

FIG. 1B shows an example of a reagent kit of a further embodiment. In FIG. 1B, 21 denotes a reagent kit, 22 denotes a first container containing a reagent containing a capture substance that binds to CDK4, 23 denotes a second container containing a reagent containing a capture substance that binds to CDK6, 24 denotes a third container containing a reagent containing a substrate, 25 denotes a packing box, and 26 denotes an attached document. In this example, the substrate is a common substrate for CDK4 and CDK6.

Figure 1C:
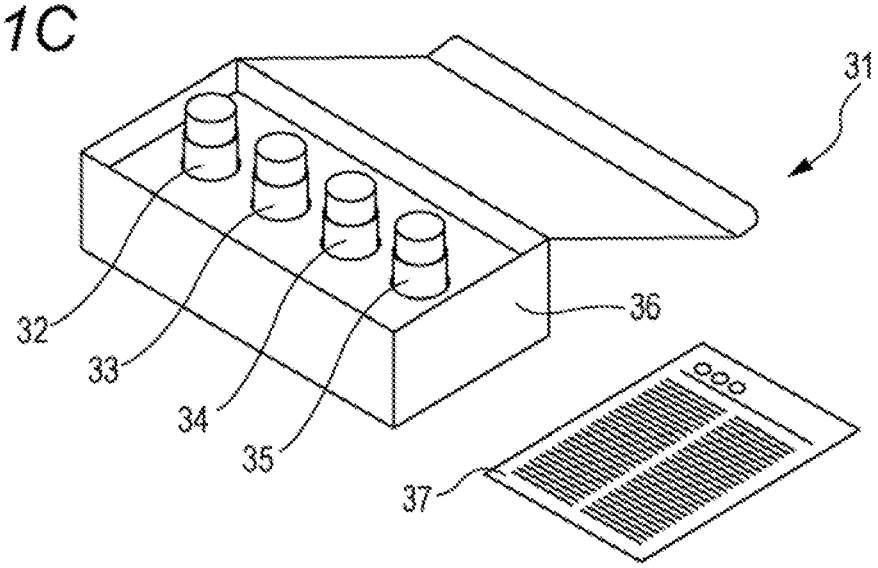
FIG. 1C is a schematic diagram showing an example of the reagent kit of the present embodiment.

FIG. 1C shows an example of a reagent kit of a further embodiment. In FIG. 1C, 31 denotes a reagent kit, 32 denotes a first container containing a reagent containing a capture substance that binds to CDK4, 33 denotes a second container containing a reagent containing a capture substance that binds to CDK6, 34 denotes a third container containing a reagent containing a capture substance that binds to CDK2, 35 denotes a fourth container containing a reagent containing a substrate, 36 denotes a packing box, and 37 denotes an attached document. In this example, the substrate is a common substrate for CDK2, CDK4 and CDK6.

It is preferable that any of the above reagent kits include a calibrator. An example of the calibrator includes a calibrator for quantifying the activity and/or expression level of CDK4 (CDK4 calibrator), a calibrator for quantifying the activity and/or expression level of CDK6 (CDK6 calibrator), or a calibrator for quantifying the activity and/or expression level of CDK2 (CDK2 calibrator). The CDK4 calibrator may include, for example, a buffer solution containing no CDK4 (negative control) and a buffer solution containing a recombinant CDK4 protein at a known concentration. The CDK6 calibrator may include, for example, a buffer solution containing no CDK6 (negative control) and a buffer solution containing a recombinant CDK6 protein at a known concentration. The CDK2 calibrator may include, for example, a buffer solution containing no CDK2 (negative control) and a buffer solution containing a recombinant CDK2 protein at a known concentration.

[6. Apparatus and Computer Program]

The scope of the present invention also includes apparatuses for carrying out the determination method of the present embodiment. Such an apparatus is a determination apparatus for sensitivity to a CDK4/6 inhibitor (hereinafter also simply referred to as "determination apparatus"). The scope of the present disclosure also includes a computer program for making a computer execute the determination method of the present embodiment. Such a computer program is a computer program for determining sensitivity to a CDK4/6 inhibitor. The scope of the present disclosure also includes a device for carrying out the acquisition method of the present embodiment. Such a device is a device for acquiring a value based on CDK activity.

Figure 2:
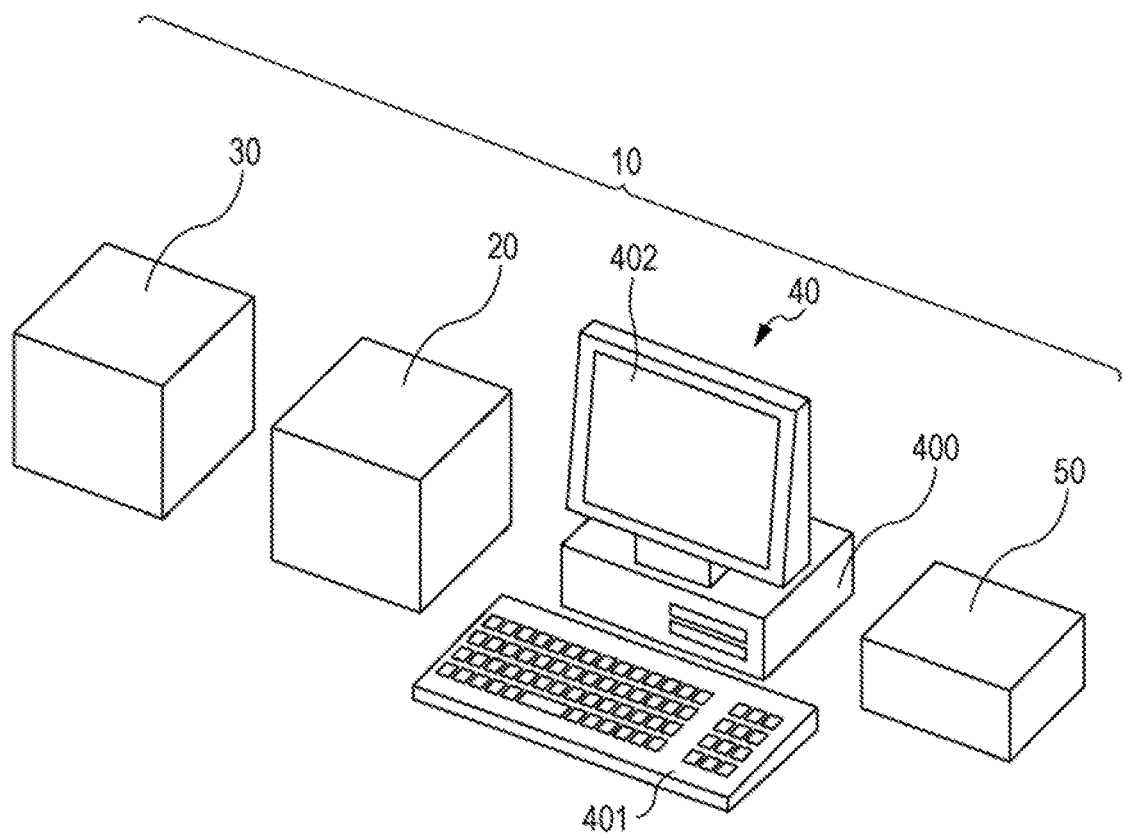
FIG. 2 is a schematic diagram showing an example of the determination apparatus of the present embodiment.

Hereinbelow, an example of the apparatus for carrying out the method of the present embodiment will be described with reference to the drawings. However, this embodiment is not limited only to the present embodiment shown in this example. FIG. 2 is a schematic view of a determination apparatus. A determination apparatus 10 shown in FIG. 2 includes a CDK activity measuring device 20, a CDK expression level measuring device 30, a printer 50, and a computer system 40 connected to the measuring devices 20 and 30, and the printer 50.

In the present embodiment, the type of CDK activity measuring device is not particularly limited, and it can be appropriately selected according to the method for measuring activity. In the example shown in FIG. 2, the CDK activity measuring device 20 is a commercially available automatic immunoassay apparatus capable of detecting a chemiluminescent signal generated by ELISA. Examples of the automatic immunoassay apparatus include HISCL (trademark)-5000 and HI-1000 manufactured by Sysmex Corporation, and the like. The CDK activity measuring device 20 is not particularly limited as long as it can detect a signal based on the labeling substance used, and it can be appropriately selected according to the type of the labeling substance. For example, when the CDK activity measuring device 20 is set with a supernatant containing a phosphorylated substrate, a solid phase for immobilizing a substrate and a phosphorylated substrate, and a detection substance that binds to a phosphorylated amino acid, the device performs an antigen-antibody reaction using each reagent to acquire a chemiluminescent signal based on an enzyme-labeled antibody specifically bound to a phosphorylation substrate, and a measured value of CDK activity is acquired from the signal. The CDK activity measuring device 20 transmits the obtained measured value of activity to the computer system 40.

In the present embodiment, the type of CDK expression level measuring device is not particularly limited, and it can be appropriately selected according to the method for measuring expression level. In the example shown in FIG. 2, the CDK expression level measuring device 30 is a commercially available CCD imager capable of detecting a chemiluminescent signal generated by Western blot. The CDK expression level measuring device 30 is not particularly limited as long as it can detect a signal based on the labeling substance used, and it can be appropriately selected according to the type of the labeling substance. For example, when a membrane that has been subjected to Western blot using an anti-CDK antibody and an enzyme-labeled antibody is set in the CDK expression level measuring device 30, the device acquires a chemiluminescent signal based on the enzyme-labeled antibody indirectly bound to CDK on the membrane, and a measured value of expression level of CDK is acquired from the signal. The CDK expression level measuring device 30 transmits the obtained measured value of expression level to the computer system 40.

The computer system 40 includes a computer main body 400, an input unit 401, and a display unit 402 that displays specimen information, a determination result, and the like. The computer system 40 receives the measured values of activity and expression level of CDK from the measuring devices 20 and 30. Then, a processor of the computer system 40 calculates a value based on CDK activity from the measured values of activity and expression level of CDK. In this example, the processor of the computer system 40 calculates a specific activity value of CDK. When the values of activity and expression level of CDK obtained from a sample treated with a CDK4/6 inhibitor, and the values of activity and expression level of CDK obtained from a sample not treated with a CDK4/6 inhibitor are received by each measured value, it is preferable that the processor of the computer system 40 calculates a ratio value of the specific activity of CDK.

The processor of the computer system 40 executes a computer program for determining sensitivity to a CDK4/6 inhibitor, which is installed on the hard disk 413, based on the value based on the calculated CDK activity. As shown in FIG. 2, the computer system 40 may be equipment separate from the measuring devices 20 and 30. Alternatively, the computer system 40 may be equipment including the measuring device 20 and/or 30.

Figure 3:
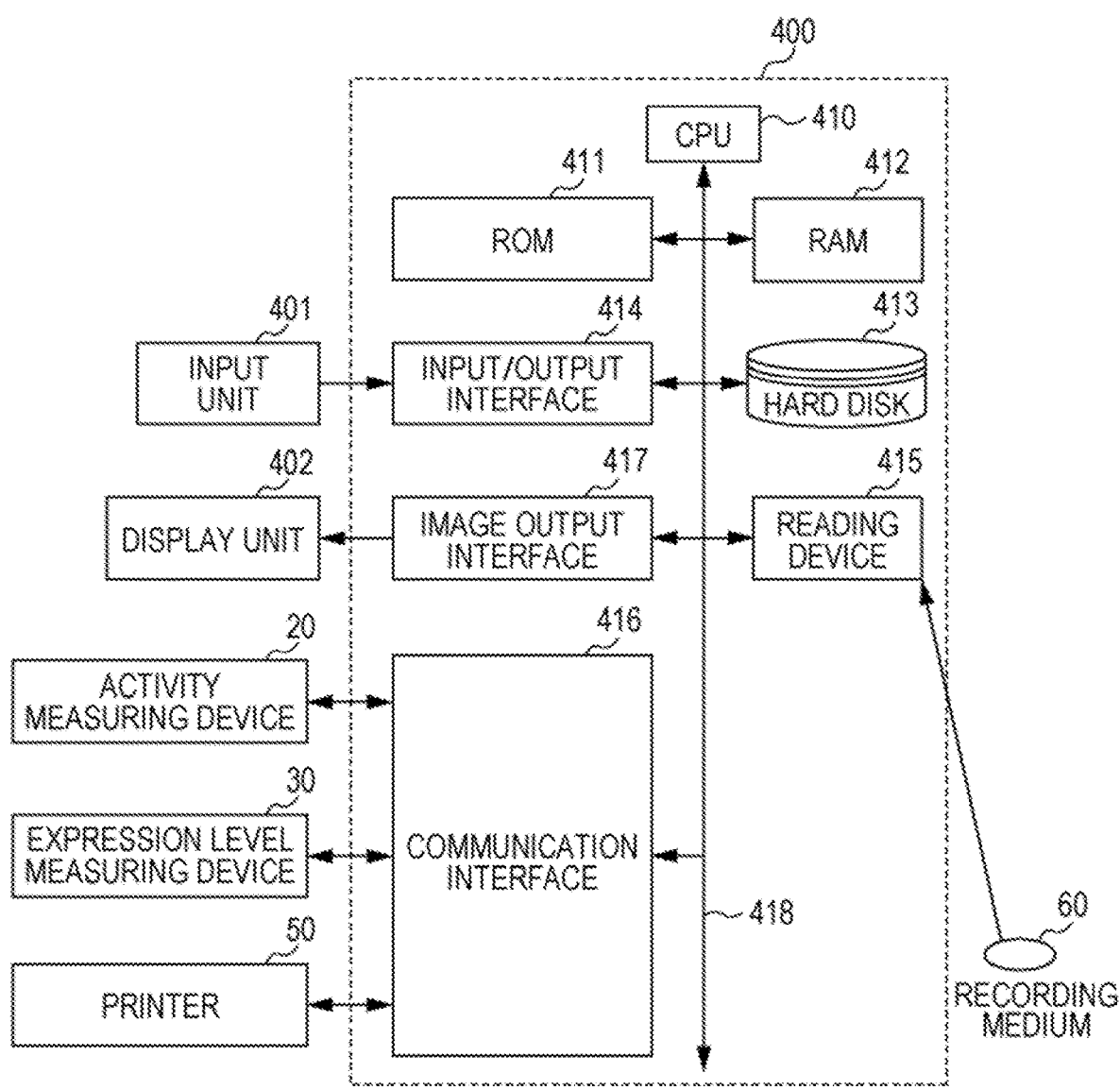
FIG. 3 is a block diagram showing a hardware configuration of the determination apparatus of the present embodiment.

With reference to FIG. 3, the computer main body 400 includes a central processing unit (CPU) 410, a read only memory (ROM) 411, a random access memory (RAM) 412, a hard disk 413, an input/output interface 414, a reading device 415, a communication interface 416, and an image output interface 417. The CPU 410, the ROM 411, the RAM 412, the hard disk 413, the input/output interface 414, the reading device 415, the communication interface 416 and the image output interface 417 are data-communicably connected by a bus 418. The measuring devices 20 and 30 and the printer 50 are communicably connected to the computer system 40 via the communication interface 416.

The CPU 410 can execute a program stored in the ROM 411 or the hard disk 413 and a program loaded in the RAM 412. The CPU 410 calculates a value based on activity of each CDK, reads a predetermined threshold level corresponding to each CDK stored in the ROM 411 or the hard disk 413, and determines whether the subject is sensitive to the CDK4/6 inhibitor. The CPU 410 outputs the determination result and displays the determination result on the display unit 402. The threshold level corresponding to the CDK may be stored in the ROM 411 or the hard disk 413 by the manufacturer in advance when the computer system is manufactured, or may be input by a user using the input unit 401 and stored in the ROM 411 or the hard disk 413.

The ROM 411 includes a mask ROM, PROM, EPROM, EEPROM, and the like. In the ROM 411, a computer program executed by the CPU 410 and data used for executing the computer program are recorded as described above. In the ROM 411, data used for a determination flow to be described later such as the predetermined threshold level corresponding to each CDK may be recorded.

The RAM 412 includes SRAM, DRAM, and the like. The RAM 412 is used for reading the program recorded in the ROM 411 and the hard disk 413. The RAM 412 is also used as a work area of the CPU 410 when these programs are executed.

The hard disk 413 has installed therein an operating system to be executed by the CPU 410, a computer program such as an application program (the computer program for determining sensitivity), and data used for executing the computer program. In the hard disk 413, data used for a determination flow to be described later such as the predetermined threshold level corresponding to each CDK may be recorded.

The reading device 415 includes a flexible disk drive, a CD-ROM drive, a DVD-ROM drive, a USB port, an SD card reader, a CF card reader, a memory stick reader, a solid state drive, and the like. The reading device 415 can read a program or data recorded on a portable recording medium 60.

The input/output interface 414 includes, for example, a serial interface such as USB, IEEE1394 and RS-232C, a parallel interface such as SCSI, IDE and IEEE1284, and an analog interface including a D/A converter, an A/D converter and the like. The input unit 401 such as a keyboard and a mouse is connected to the input/output interface 414. An operator can input various commands to the computer main body 400 through the input unit 401.

The communication interface 416 is, for example, a wireless interface conforming to a standard such as an Ethernet (registered trademark) or Bluetooth (registered trademark). The computer main body 400 can transmit print data to the printer 50 or the like through the communication interface 416. The printer 50 is, for example, a laser printer, an inkjet printer, or the like. When the communication interface 416 is a wireless interface, the computer main body 400 can transmit data to a mobile device such as a mobile phone or a tablet terminal.

The image output interface 417 is connected to the display unit 402 including an LCD, a CRT, and the like. As a result, the display unit 402 can output a video signal corresponding to the image data coming from the CPU 410. The display unit 402 displays an image (screen) according to the input video signal.

Figure 4A:
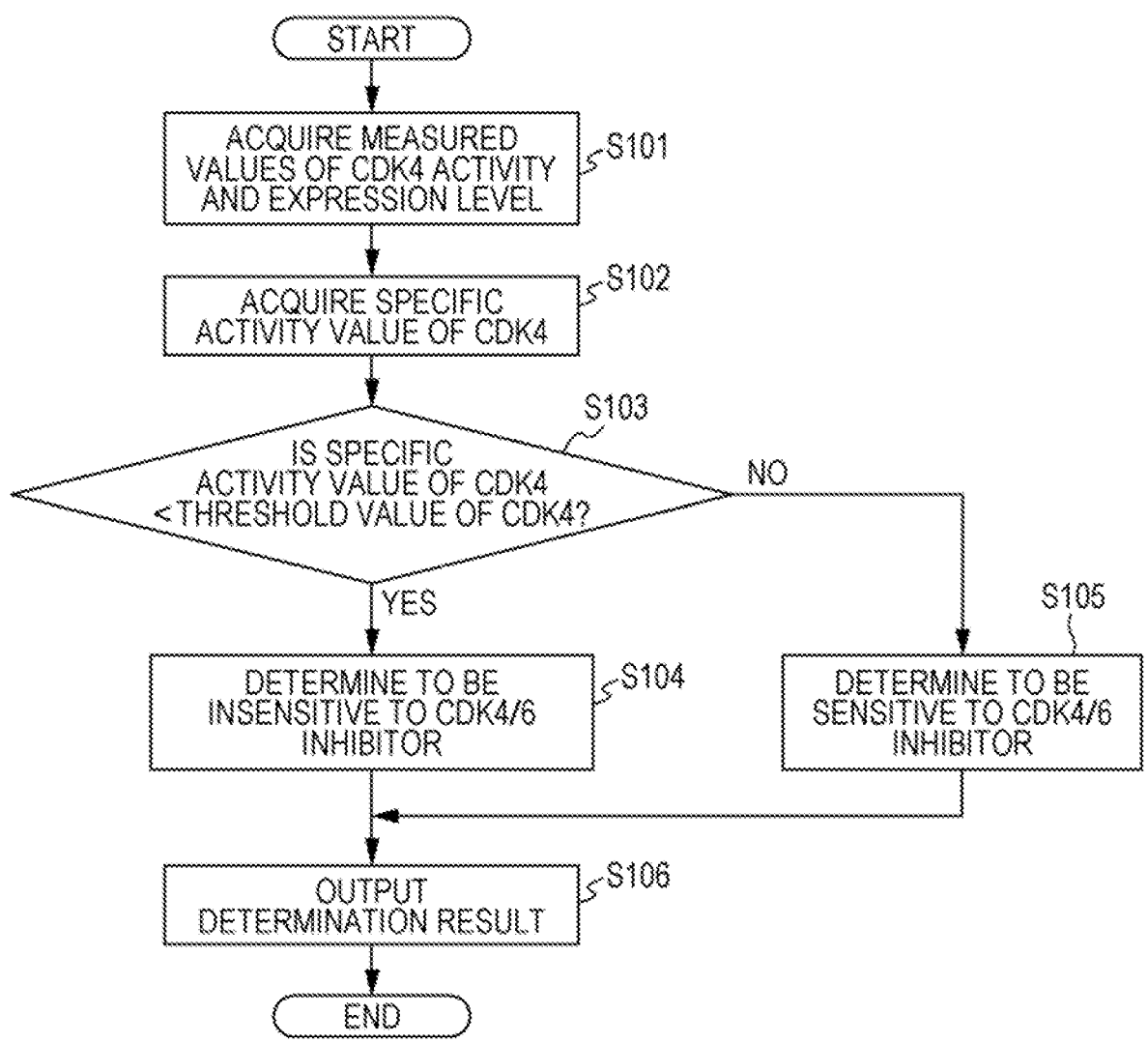
FIG. 4A is a flowchart for determining sensitivity to a CDK4/6 inhibitor using the determination apparatus of the present embodiment.

With reference to FIG. 4A, a determination flow of sensitivity to a CDK4/6 inhibitor executed by the determination apparatus 10 will be described. Here, a case where a specific activity value of CDK4 is acquired and determination is made using the acquired value will be described as an example. However, the present embodiment is not limited only to this example. Instead of the specific activity value of CDK4, a specific activity value of CDK6 may be acquired. Instead of the specific activity value, a ratio value of the specific activity may be acquired.

In step S101, the CPU 410 acquires a measured value of CDK4 activity from the measuring device 20, the CPU 410 acquires a measured value of expression level of CDK4 from the measuring device 30, and the CPU 410 stores them in the hard disk 413. In step S102, the CPU 410 calculates a specific activity value of CDK4 by dividing the measured value of CDK4 activity by the measured value of expression level of CDK4, and the CPU 410 stores the value in the hard disk 413. In step S103, the CPU 410 compares the specific activity value of CDK4 with the threshold level of CDK4 stored in the hard disk 413. When the specific activity value of CDK4 is less than the threshold level of CDK4, the process proceeds to step S104. In step S104, the CPU 410 stores a determination result that the subject is insensitive to the CDK4/6 inhibitor in the hard disk 413.

On the other hand, when the specific activity value of CDK4 is greater than or equal to the threshold level of CDK4 in step S103, the process proceeds to step S105. In step S105, the CPU 410 stores a determination result that the subject is sensitive to the CDK4/6 inhibitor in the hard disk 413. In step S106, the CPU 410 outputs the determination result. For example, the CPU 410 displays the determination result on the display unit 402, the CPU 410 prints the determination result with the printer 50, or the CPU 410 transmits the determination result to a mobile device such as a mobile phone or a tablet terminal. As a result, it is possible to provide doctors and the like with information to assist determination of sensitivity to the CDK4/6 inhibitor.

With reference to FIG. 4B, a determination flow of sensitivity to a CDK4/6 inhibitor executed by the determination apparatus 10 will be described. Here, a case where specific activity values of CDK4 and CDK6 are acquired and determination is made using the acquired value will be described as an example. However, the present embodiment is not limited only to this example. Instead of the specific activity value of each CDK, a ratio value of the specific activity may be acquired.

In step S201, the CPU 410 acquires measured values of CDK4 and CDK6 activities from the measuring device 20, the CPU 410 acquires measured values of expression levels of CDK4 and CDK6 from the measuring device 30, and the CPU 410 stores them in the hard disk 413. In step S202, the CPU 410 calculates a specific activity value of CDK4, and the CPU 410 stores it in the hard disk 413 in the same manner as in step S102. The CPU 410 calculates a specific activity value of CDK6, and the CPU 410 stores it in the hard disk 413. In step S203, the CPU 410 compares the specific activity value of CDK4 with the first threshold level stored in the hard disk 413, and the CPU 410 compares the specific activity value of the CDK6 with the second threshold level stored in the hard disk 413. The first threshold level is a threshold level corresponding to CDK4, and the second threshold level is a threshold level corresponding to CDK6. In step S203, when the specific activity value of CDK4 is less than the first threshold level and the specific activity value of CDK6 is less than the second threshold level, the process proceeds to step S204. In step S204, the CPU 410 stores a determination result that the subject is insensitive to the CDK4/6 inhibitor in the hard disk 413.

When the specific activity value of CDK4 and the specific activity value of CDK6 do not satisfy the conditions of step S203, the process proceeds to step S205. In step S205, when the specific activity value of CDK4 is greater than or equal to the first threshold level and the specific activity value of CDK6 is greater than or equal to the second threshold level, the process proceeds to step S206. In step S206, the CPU 410 stores a determination result that the subject is sensitive to the CDK4/6 inhibitor in the hard disk 413. On the other hand, when the specific activity value of CDK4 and the specific activity value of CDK6 do not also satisfy the conditions of step S205, the process proceeds to step S207. In step S207, the CPU 410 stores a determination result that the subject has a moderate sensitivity to the CDK4/6 inhibitor in the hard disk 413. In step S208, the CPU 410 outputs the determination result. For example, the CPU 410 displays the determination result on the display unit 402, the CPU 410 prints the determination result with the printer 50, or the CPU 410 transmits the determination result to a mobile device. As a result, it is possible to provide doctors and the like with information to assist determination of sensitivity to the CDK4/6 inhibitor. In this example, the order of processes in steps S203 and S205 can be changed.

With reference to FIG. 4C, a determination flow of sensitivity to a CDK4/6 inhibitor executed by the determination apparatus 10 will be described. Here, a case where specific activity values of CDK4 and CDK2 are acquired and determination is made using the acquired value will be described as an example. However, the present embodiment is not limited only to this example. Instead of the specific activity value of CDK4, a specific activity value of CDK6 may be acquired. Instead of the specific activity value of each CDK, a ratio value of the specific activity may be acquired.

In step S301, the CPU 410 acquires measured values of CDK4 and CDK2 activities from the measuring device 20, the CPU 410 acquires measured values of expression levels of CDK4 and CDK2 from the measuring device 30, and the CPU 410 stores them in the hard disk 413. In step S302, the CPU 410 calculates a specific activity value of CDK4, and the CPU 410 stores it in the hard disk 413 in the same manner as in step S102. The CPU 410 calculates a specific activity value of CDK2, and the CPU 410 stores it in the hard disk 413. In step S303, the CPU 410 compares the specific activity value of CDK4 with the first threshold level stored in the hard disk 413, and the CPU 410 compares the specific activity value of the CDK2 with the second threshold level stored in the hard disk 413. The first threshold level is a threshold level corresponding to CDK4, and the second threshold level is a threshold level corresponding to CDK2. In step S303, when the specific activity value of CDK4 is less than the first threshold level and the specific activity value of CDK2 is greater than or equal to the second threshold level, the process proceeds to step S304. In step S304, the CPU 410 stores a determination result that the subject is insensitive to the CDK4/6 inhibitor in the hard disk 413.

When the specific activity value of CDK4 and the specific activity value of CDK2 do not satisfy the conditions of step S303, the process proceeds to step S305. In step S305, when the specific activity value of CDK4 is greater than or equal to the first threshold level and the specific activity value of CDK2 is less than the second threshold level, the process proceeds to step S306. In step S306, the CPU 410 stores a determination result that the subject is sensitive to the CDK4/6 inhibitor in the hard disk 413. On the other hand, when the specific activity value of CDK4 and the specific activity value of CDK2 do not also satisfy the conditions of step S305, the process proceeds to step S307. In step S307, the CPU 410 stores a determination result that the subject has a moderate sensitivity to the CDK4/6 inhibitor in the hard disk 413. In step S308, the CPU 410 outputs the determination result. For example, the CPU 410 displays the determination result on the display unit 402, the CPU 410 prints the determination result with the printer 50, or the CPU 410 transmits the determination result to a mobile device. As a result, it is possible to provide doctors and the like with information to assist determination of sensitivity to the CDK4/6 inhibitor. In this example, the order of processes in steps S303 and S305 can be changed.

With reference to FIG. 4D, a determination flow of sensitivity to a CDK4/6 inhibitor executed by the determination apparatus 10 will be described. Here, a case where specific activity values of CDK4, CDK6 and CDK2 are acquired and determination is made using the acquired value will be described as an example. However, the present embodiment is not limited only to this example. Instead of the specific activity value of each CDK, a ratio value of the specific activity may be acquired.

In step S401, the CPU 410 acquires measured values of CDK4, CDK6 and CDK2 activities from the measuring device 20, the CPU 410 acquires measured values of expression levels of CDK4, CDK6 and CDK2 from the measuring device 30, and the CPU 410 stores them in the hard disk 413. In step S402, the CPU 410 calculates the specific activity value of CDK4, and the CPU 410 stores it in the hard disk 413 in the same manner as in step S102. The CPU 410 calculates a specific activity value of CDK6 and a specific activity value of CDK2, and the CPU 410 stores them in the hard disk 413. In step S403, the CPU 410 compares the specific activity value of CDK4 with the first threshold level stored in the hard disk 413, the CPU 410 compares the specific activity value of CDK6 with the second threshold level stored in the hard disk 413, and the CPU 410 compares the specific activity value of the CDK2 with the third threshold level stored in the hard disk 413. The first threshold level is a threshold level corresponding to CDK4, and the second threshold level is a threshold level corresponding to CDK6. The third threshold level is a threshold level corresponding to CDK2.

In step S403, when the specific activity value of CDK4 is less than the first threshold level, the specific activity value of CDK6 is less than the second threshold level, and the specific activity value of CDK2 is greater than or equal to the third threshold level, the process proceeds to step S404. In step S404, the CPU 410 stores a determination result that the subject is insensitive to the CDK4/6 inhibitor in the hard disk 413.

When the specific activity value of CDK4, the specific activity value of CDK6 and the specific activity value of CDK2 do not satisfy the conditions of step S403, the process proceeds to step S405. In step S405, when the specific activity value of CDK4 is greater than or equal to the first threshold level, the specific activity value of CDK6 is greater than or equal to the second threshold level, and the specific activity value of CDK2 is less than the third threshold level, the process proceeds to step S406. In step S406, the CPU 410 stores a determination result that the subject is sensitive to the CDK4/6 inhibitor in the hard disk 413. On the other hand, when the specific activity value of CDK4, the specific activity value of CDK6 and the specific activity value of CDK2 do not also satisfy the conditions of step S405, the process proceeds to step S407. In step S407, the CPU 410 stores a determination result that the subject has a moderate sensitivity to the CDK4/6 inhibitor in the hard disk 413. In step S408, the CPU 410 outputs the determination result. For example, the CPU 410 displays the determination result on the display unit 402, the CPU 410 prints the determination result with the printer 50, or the CPU 410 transmits the determination result to a mobile device. As a result, it is possible to provide doctors and the like with information to assist determination of sensitivity to the CDK4/6 inhibitor. In this example, the order of processes in steps S403 and S405 can be changed.

Figure 5:
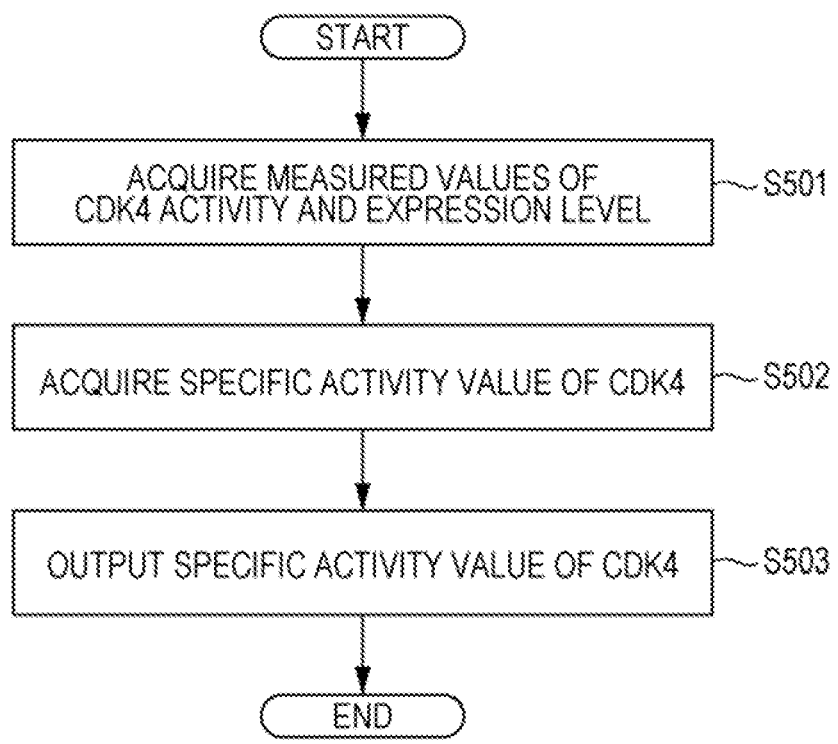
FIG. 5 is a flowchart showing a processing procedure by a device for acquiring a value based on CDK activity.

With reference to FIG. 5, a processing procedure executed by a device 10 for acquiring a value based on CDK activity will be described. Here, the measured value of CDK4 activity is acquired from the measuring device 20, the measured value of expression level of CDK4 is acquired from the measuring device 30, and a case where the specific activity of CDK4 is acquired as a value based on CDK activity from the acquired measured value will be described as an example. However, the present embodiment is not limited only to this example. Instead of the specific activity value of CDK4, a specific activity value of CDK6 may be acquired. In a further embodiment, the specific activity value of CDK4 or CDK6 and the specific activity value of CDK2 may be acquired. Alternatively, the specific activity values of CDK4, CDK6 and CDK2 may be acquired. Instead of the specific activity value of each CDK, a ratio value of the specific activity may be acquired.

In step S501, the CPU 410 acquires a measured value of CDK4 activity from the measuring device 20, the CPU 410 acquires a measured value of expression level of CDK4 from the measuring device 30, and the CPU 410 stores them in the hard disk 413. In step S502, the CPU 410 calculates a specific activity value of CDK4 by dividing the measured value of CDK4 activity by the measured value of expression level of CDK4, and the CPU 410 stores the value in the hard disk 413. In step S503, the CPU 410 outputs the acquired specific activity value of CDK4. For example, the CPU 410 displays the determination result on the display unit 402, the CPU 410 prints the determination result with the printer 50, or the CPU 410 transmits the determination result to a mobile device. A predetermined threshold level corresponding to each CDK may be outputted together with the acquired value based on the CDK activity.

The value based on the CDK activity obtained by the acquisition device is information suggesting sensitivity of the subject to the CDK4/6 inhibitor, by comparison with the predetermined threshold level corresponding to each CDK. Specifically, it is the same as that described for the acquisition method of the present embodiment.

Hereinafter, the present disclosure will be described in more detail by examples, but the present disclosure is not limited to these examples.

EXAMPLES

Example 1

Expression levels and enzymatic activities of CDK2, CDK4 and CDK6 in each of lysate samples of untreated breast cancer cell line and breast cancer cell line treated with a CDK4/6 inhibitor (palbociclib) were measured. The obtained measurement data of expression levels and activities was compared with 50% inhibitory concentration (IC50) which is an index of drug effect, and the relationship between them was verified.
(1) Determination of IC50

Six types of breast cancer cell lines, T47D, MCF7, HCC1500, CAMA-1, DU4475 and MDA-MB-231, were used. T47D, MCF7, HCC1500 and CAMA-1 are HER2-negative/ER-positive breast cancer cell lines, and DU4475 and MDA-MB-231 are cell lines derived from triple negative breast cancer (TNBC). Each cell line was seeded in a 96-well plate at $2.5 \times 10^3$ cells/0.1 mL/well, and palbociclib was added at a concentration of 100 pM, 1 nM, 10 nM, 100 nM, 1 μM, 10 μM or 100 μM. Each cell line to which dimethyl sulfoxide (DMSO) was added instead of palbociclib was defined as an untreated breast cancer cell line. After 48 hours, an inhibitory effect of palbociclib was analyzed based on the number of viable cells in a cytotoxicity test using WST-8 (DOJINDO LABORATORIES). In the analysis, the survival rate of the untreated cell line was set to 100%. The IC50 value was calculated from the normalized data by performing curve fitting using KaleidaGraph 4.0. Table 1 shows the IC50 values of each cell line.

TABLE 1

| Cell line | IC50 (nM) |
| --- | --- |
| T47D | 202 |
| MCF7 | 767 |
| HCC1500 | 5,360 |
| CAMA-1 | 888 |
| DU4475 | >10,000 |
| MDA-MB-231 | 475 |
| Median | 767 |
| Average | 1,538 |
| SD | 2,153 |

As shown in Table 1, T47D, MDA-MB-231 and MCF7 were found to be breast cancer cell lines relatively having a sensitivity to a CDK4/6 inhibitor. On the other hand, CAMA-1 was found to be a breast cancer cell line relatively having a resistance to a CDK4/6 inhibitor, and HCC1500 and DU4475 were found to be breast cancer cell lines having a strong resistance to a CDK4/6 inhibitor. Hereinafter, T47D, MDA-MB-231 and MCF7 are also referred to as "sensitive group", and CAMA-1, HCC1500 and DU4475 are also referred to as "resistant group".
(2) Preparation of Lysate Sample Palbociclib was added to each of the six breast cancer cell lines at a concentration of 426 nM. Each cell line to which DMSO was added instead of palbociclib was defined as an untreated breast cancer cell line. After 48 hours, cells were recovered. A cell solubilization buffer was added to a cell pellet to be $5 \times 10^7$ cells/mL to lyse the cells, and the supernatant was recovered by centrifugation to obtain a cell lysate (hereinafter also referred to as a "lysate sample"). The composition of the cell solubilization buffer was as follows.
[Composition of Cell Solubilization Buffer]
 50 mM Tris-HCl (pH 7.4)
 150 mM NaCl 5 mM EDTA (pH 8.0)
50 mM NaF
1 mM Orthovanadic acid
0.10% NP-40
10% Glycerol
1 mM DTT Complete Protease Inhibitor Cocktail (Roche)

(3) Measurement of Expression Level

The expression levels of CDK2, CDK4 and CDK6 were measured by Western blot as follows. Samples for electrophoresis (1 mg/mL lysate sample, 2×sample buffer and 10% 2-mercaptoethanol) were prepared from each lysate sample obtained in the above (2). Each of samples for electrophoresis (10 µL/lane) was electrophoresed on a polyacrylamide gel. To quantitatively analyze the expression levels, recombinant CDK proteins (rCDK2, rCDK4 and rCDK6) were electrophoresed at 5.0 ng, 2.5 ng, 1.0 ng, 0.75 ng, 0.5 ng and 0.2 ng as standard proteins. The gel after electrophoresis was transferred to a membrane by a conventional method, and a primary reaction was performed using an anti-CDK2 antibody, an anti-CDK4 antibody, and an anti-CDK6 antibody. Then, a secondary reaction was performed using an HRP-labeled antibody, and further reacted with SuperSignal West Femto Substrate (Thermo Fisher), and a chemiluminescent signal was detected with an X-ray film. The blot was quantitatively analyzed by Image Lab 5.2.1 (Bio Rad) to calculate the expression levels (nmol/L) of CDK2, CDK4 and CDK6 in each lysate sample. Table 2 shows the expression levels of CDK2, CDK4 and CDK6 in each cell line. In the column of "drug treatment" in the table, "0 h" indicates that it has not been treated with palbociclib, and "48 h" indicates that it has been treated with palbociclib for 48 hours.

TABLE 2

| Cell line | Drug treatment | Expression level (nmol/L) | | |
|---|---|---|---|---|
| | | CDK2 | CDK4 | CDK6 |
| T47D | 0 h | 15.6 | 30.9 | 0.6 |
| | 48 h | 5.7 | 18.8 | 0.7 |
| MCF7 | 0 h | 12.1 | 57.3 | 3.3 |
| | 48 h | 3.0 | 39.4 | 4.3 |
| HCC1500 | 0 h | 6.5 | 14.0 | 0.3 |
| | 48 h | 2.9 | 12.7 | 0.4 |
| CAMA-1 | 0 h | 7.4 | 25.5 | 0.4 |
| | 48 h | 2.8 | 18.9 | 0.4 |
| DU4475 | 0 h | 13.8 | 14.2 | 28.5 |
| | 48 h | 12.3 | 16.6 | 60.9 |
| MDA-MB-231 | 0 h | 6.9 | 16.7 | 20.0 |
| | 48 h | 3.0 | 20.7 | 20.1 |

(4) Activity Measurement
(4.1) Phosphorylation Reaction by CDK

The CDK2, CDK4 and CDK6 activities were measured by reacting each CDK captured on beads via an antibody with a substrate peptide in the presence of ATP, and measuring the amount of the generated phosphorylated substrate peptide. Specifically, it was performed as follows. An anti-CDK2 antibody, an anti-CDK4 antibody, and an anti-CDK6 antibody were each mixed with protein G-immobilized beads to prepare antibody-immobilized beads. A CDK substrate peptide was prepared with reference to EP 3 404 038 A1. The N-terminal amino acid residue of this substrate peptide was biotinylated with EZ-Link (trademark) Amine-PEG11-Biotin (Thermo Fisher). The prepared antibody-immobilized beads and each lysate sample (30 µL) obtained in the above (2) were mixed and reacted at 4° C. for 1 hour with stirring. After the reaction, the supernatant was removed, the antibody-immobilized beads were mixed with a substrate solution (40 µL) containing the CDK substrate peptide, and the mixture was reacted at 42° C. for 1 hour with stirring. After the reaction, the supernatant was recovered to obtain a solution containing a phosphorylated substrate peptide (phosphorylated product). The composition of the substrate solution was as follows.

[Composition of Substrate Solution]
25 mM HEPES-NaOH (pH 7.4)
30 mM $MgCl_2$
32 mM ATP
6 µg/mL Biotinylated substrate peptide (Y42)
0.2% LIPIDURE (trademark)-BL103 (NOF Corporation)
0.0075% Antifoaming agent (4.2) Activity Measurement Using the recovered phosphorylated product as a sample, the amount of phosphorylated substrate peptide was measured as CDK activity. The measurement was performed by Automated Immunoassay System HISCL (Sysmex Corporation). This measurement is based on ELISA on magnetic particles. The phosphorylated product (30 µL) and a HISCL R2 reagent (a suspension containing streptavidin-immobilized magnetic particles: 30 µL) (Sysmex Corporation) were mixed. The magnetic particles in the obtained mixed solution were magnetically collected to remove the supernatant, and a HISCL washing solution (300 µL) was added to wash the magnetic particles. The supernatant was removed, and an R3 reagent (a mixture of a rabbit anti-phosphorylated (serine/threonine) antibody and an alkaline phosphatase (ALP)-labeled anti-rabbit IgG antibody: 100 µL) was added to the magnetic particles to react. After the reaction, the magnetic particles were magnetically collected to remove the supernatant, and a HISCL washing solution (300 µL) was added to wash the magnetic particles. The supernatant was removed, and a HISCL R4 reagent (50 µL) (Sysmex Corporation) containing a measurement buffer solution, and a HISCL R5 reagent (100 µL) (Sysmex Corporation) containing ALP substrate CDP-Star (registered trademark) (Applied Biosystems) were added to the magnetic particles and reacted, and the luminescence count was measured. Table 3 shows the measured values of activity of each CDK. Table 3 also shows the measured values of expression levels and specific activity values obtained in the above (3). The specific activity values were calculated by the following equation.

[Specific activity value of CDK]=[Measured value of CDK activity]/[Measured value of expression level of CDK]

TABLE 3

| Cell line | Drug treatment | CDK2 | | | CDK4 | | | CDK6 | | |
|---|---|---|---|---|---|---|---|---|---|---|
| | | Activity | Expression level | Specific activity | Activity | Expression level | Specific activity | Activity | Expression level | Specific activity |
| T47D | 0 h | 8.1 | 15.6 | 0.52 | 12.8 | 30.9 | 0.41 | 14.9 | 0.6 | 24.33 |
| | 48 h | 2.1 | 5.7 | 0.36 | 39.8 | 18.8 | 2.12 | 39.7 | 0.7 | 59.94 |

TABLE 3-continued

| Cell line | Drug treatment | CDK2 | | | CDK4 | | | CDK6 | | |
| --- | --- | --- | --- | --- | --- | --- | --- | --- | --- | --- |
| | | Activity | Expression level | Specific activity | Activity | Expression level | Specific activity | Activity | Expression level | Specific activity |
| MDA-MB-231 | 0 h | 6.2 | 6.9 | 0.89 | 3.8 | 16.7 | 0.23 | 8.9 | 20.0 | 0.44 |
| | 48 h | 0.7 | 3.0 | 0.24 | 9.5 | 20.7 | 0.46 | 20.9 | 20.1 | 1.04 |
| MCF7 | 0 h | 8.0 | 12.1 | 0.66 | 34.8 | 57.3 | 0.61 | 19.7 | 3.3 | 5.99 |
| | 48 h | 1.6 | 3.0 | 0.53 | 65.2 | 39.4 | 1.65 | 66.7 | 4.3 | 15.43 |
| CAMA-1 | 0 h | 1.3 | 7.4 | 0.17 | 5.7 | 25.5 | 0.22 | 16.8 | 0.4 | 46.76 |
| | 48 h | 0.7 | 2.8 | 0.25 | 3.8 | 18.9 | 0.20 | 19.3 | 0.4 | 44.15 |
| HCC1500 | 0 h | 0.7 | 6.5 | 0.11 | 5.7 | 14.0 | 0.41 | 11.3 | 0.3 | 36.43 |
| | 48 h | 0.7 | 2.9 | 0.25 | 4.1 | 12.7 | 0.33 | 13.6 | 0.4 | 36.80 |
| DU4475 | 0 h | 13.4 | 13.8 | 0.97 | 5.0 | 14.2 | 0.35 | 19.6 | 28.5 | 0.69 |
| | 48 h | 14.5 | 12.3 | 1.17 | 9.1 | 16.6 | 0.55 | 21.5 | 60.9 | 0.35 |

(5) Determination of Sensitivity to CDK4/6 Inhibitor

Based on the results shown in Table 3, at 48 hours after the addition of the CDK4/6 inhibitor to the cells, the degree of change in values of expression level and specific activity of each CDK was examined. Specifically, as an index indicating the change in values of expression level and specific activity of each CDK, the ratio (48 h/0 h) of the value after treatment (48 h) to the value of untreated (0 h) was calculated. The calculated ratio was compared with the IC50, and the relationship between them was verified. Table 4 shows the ratio of the measured value of expression level of each CDK, and Table 5 shows the ratio of specific activity value of each CDK.

TABLE 4

| | | Ratio value of expression level (48 h/0 h) | | |
| --- | --- | --- | --- | --- |
| Cell line | IC50 | CDK2 | CDK4 | CDK6 |
| T47D | 202 | 0.36 | 0.61 | 1.08 |
| MDA-MB-231 | 475 | 0.43 | 1.24 | 1.00 |
| MCF7 | 767 | 0.25 | 0.69 | 1.32 |
| CAMA-1 | 888 | 0.38 | 0.74 | 1.22 |
| HCC1500 | 5,360 | 0.44 | 0.91 | 1.20 |
| DU4475 | 10,000 | 0.89 | 1.17 | 2.14 |
| Correlation coefficient | | 0.897 | 0.517 | 0.874 |

TABLE 5

| | | Ratio value of specific activity (48 h/0 h) | | |
| --- | --- | --- | --- | --- |
| Cell line | IC50 | CDK2 | CDK4 | CDK6 |
| T47D | 202 | 0.7 | 5.1 | 2.5 |
| MDA-MB-231 | 475 | 0.3 | 2.0 | 2.3 |
| MCF7 | 767 | 0.8 | 2.7 | 2.6 |
| CAMA-1 | 888 | 1.5 | 0.9 | 0.9 |
| HCC1500 | 5,360 | 2.3 | 0.8 | 1.0 |
| DU4475 | 10,000 | 1.2 | 1.5 | 0.5 |

As shown in Table 4, a correlation was observed between the ratio of expression levels of CDK2 and CDK6 and the IC50. However, it has been difficult to set a threshold level that can distinguish between the sensitive group and the resistant group. No correlation was observed between the expression level of CDK4 and the IC50. These suggested that it is not appropriate to use the ratio of expression levels of CDK2, CDK4 and CDK6 as an index for determining sensitivity to a CDK4/6 inhibitor.

As shown in Table 5, in the sensitive groups T47D, MDA-MB-231 and MCF7, the ratio value of specific activity of CDK2 tended to be low, and the ratio values of specific activities of CDK4 and CDK6 tended to be high. On the other hand, in the resistant groups CAMA-1, HCC1500 and DU4475, the ratio value of specific activity of CDK2 tended to be high, and the ratio values of specific activities of CDK4 and CDK6 tended to be low. From this result, as a threshold level corresponding to the ratio value of specific activity of CDK4, for example, a value higher than 1.5 and less than 2.0 can be set. As a threshold level corresponding to the ratio value of specific activity of CDK6, for example, a value higher than 1.0 and less than 2.3 can be set. As a threshold level corresponding to the ratio value of specific activity of CDK2, for example, a value higher than 0.8 and less than 1.2 can be set. The fact that the ratio values of specific activities of CDK4 and CDK6 were high in the cell line sensitive to a CDK4/6 inhibitor, and the ratio values of specific activities of CDK4 and CDK6 were low in the cell line insensitive to a CDK4/6 inhibitor was opposite to a result expected from the IC50 shown in Table 1.

From the above, it was suggested that change in the specific activity of CDK2, CDK4 and CDK6 after adding a CDK4/6 inhibitor to a lysate sample of cancer cells or tumor tissues can be used as an index for determining sensitivity to a CDK4/6 inhibitor. For example, the following determination could be made from the results in Table 5. When the ratio value of specific activity of CDK2 was used as an index, the sensitive group and the resistant group could be stratified by setting the threshold level to 1.2. Similarly, when the ratio values of specific activities of CDK4 and CDK6 were used as indexes, the sensitive group and the resistant group could be stratified by respectively setting the threshold levels to 1.5 and 1.0.

Example 2

Whether the stratification of the sensitive group and the resistant group can be favorably performed was examined by combining the ratio value of specific activity of CDK4 or CDK6 shown in Table 5 and the ratio value of specific activity of CDK2. Specifically, the ratio values of specific activities of each cell line were plotted on a coordinate plane taking the ratio value of specific activity of CDK4 or CDK6 on a vertical axis and taking the ratio value of specific activity of CDK2 on a horizontal axis. The results are shown in FIGS. 6 and 7.

Figure 6:
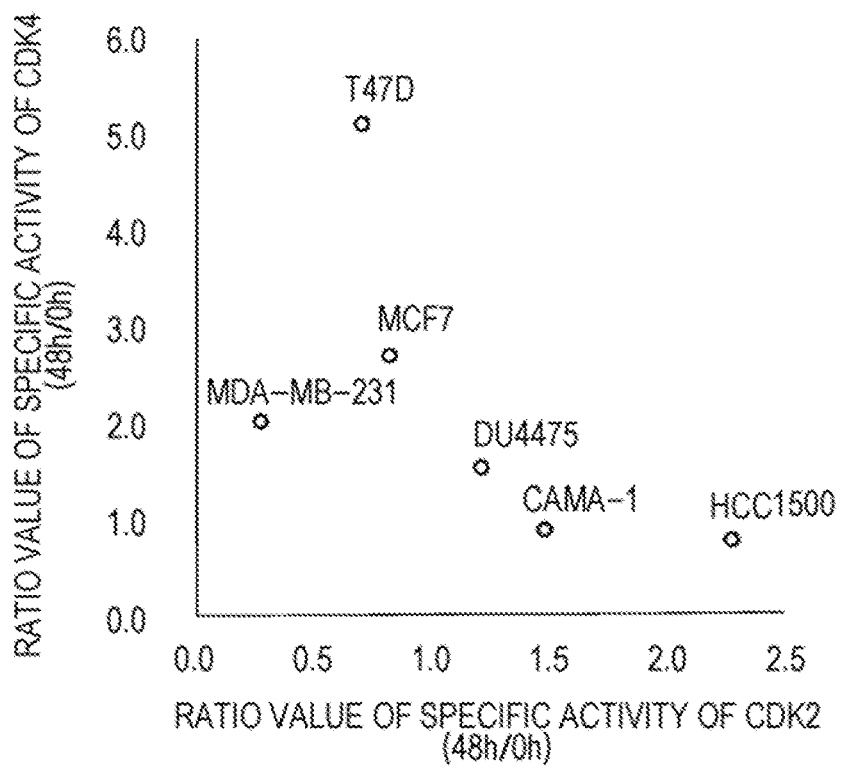
FIG. 6 is a graph in which ratio values of specific activities of CDK4 and ratio values of specific activities of CDK2 of various breast cancer cell lines are plotted.
Figure 7:
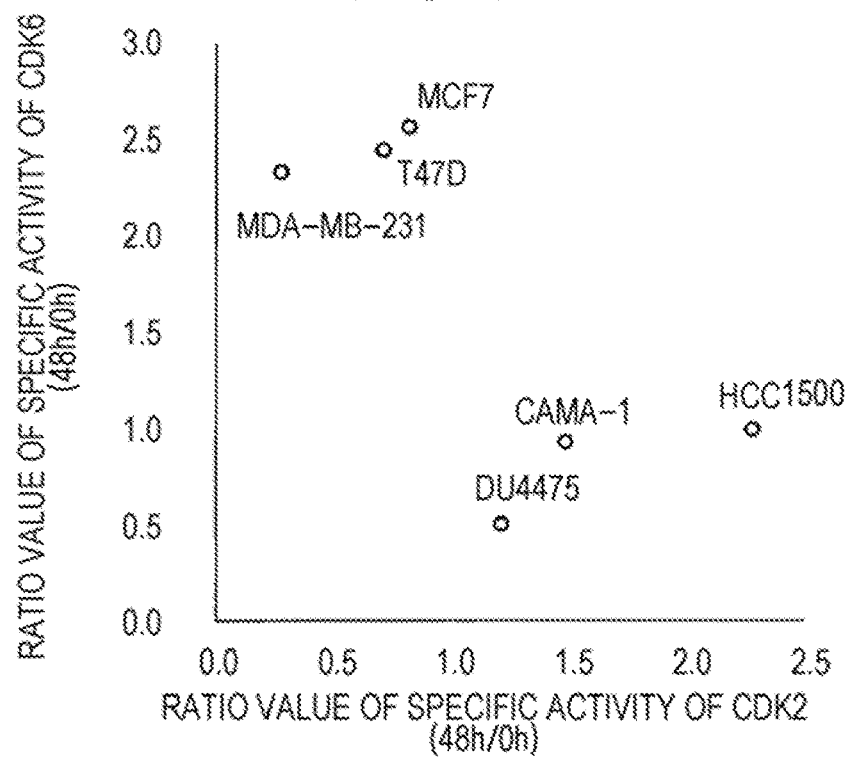
FIG. 7 is a graph in which ratio values of specific activities of CDK6 and ratio values of specific activities of CDK2 of various breast cancer cell lines are plotted.

As shown in FIGS. 6 and 7, the sensitive group appeared in an area where the ratio value of specific activity of CDK4 or CDK6 was high and the ratio value of specific activity of CDK2 was low. On the other hand, the resistant group appeared in an area where the ratio value of specific activity of CDK4 or CDK6 was low and the ratio value of specific activity of CDK2 was high. Therefore, it was suggested that the sensitive group and the resistant group can be more clearly stratified by combining the ratio value of specific activity of CDK4 or CDK6 with the ratio value of specific activity of CDK2.

What is claimed is:

1. A method for determining sensitivity to a CDK4/6 inhibitor, comprising the steps of:
   providing a first aliquot of a sample collected from a subject and a second aliquot of the sample,
   treating the second aliquot with the CDK4/6 inhibitor in vitro, wherein the first aliquot is an aliquot not treated with the CDK4/6 inhibitor,
   acquiring a first specific activity value which is a specific activity of a first CDK in the first aliquot, and a second specific activity value which is a specific activity of the first CDK in the second aliquot, and
   determining that the subject is insensitive to the CDK4/6 inhibitor when a ratio value of the second specific activity value to the first specific activity value is less than a predetermined threshold level, or a ratio value of the first specific activity value to the second specific activity value is greater than or equal to the predetermined threshold level,
   wherein the first CDK is CDK4 or CDK6.

2. The determination method according to claim 1, wherein
   in the acquisition step, a third specific activity value which is a specific activity of a second CDK in the first aliquot and a fourth specific activity value which is a specific activity of the second CDK in the second aliquot are further acquired,
   in the determination step,
     when the ratio value of the second specific activity value to the first specific activity value is less than a first threshold level, and a ratio value of the fourth specific activity value to the third specific activity value is greater than or equal to a second threshold level, or
     when the ratio value of the first specific activity value to the second specific activity value is greater than or equal to the first threshold level, and a ratio value of the third specific activity value to the fourth specific activity value is less than the second threshold level, the subject is determined to be insensitive to the CDK4/6 inhibitor, and
   the second CDK is CDK2.

3. The determination method according to claim 1, wherein
   in the acquisition step, a third specific activity value which is a specific activity of a second CDK in the first aliquot, a fourth specific activity value which is a specific activity of the second CDK in the second aliquot, a fifth specific activity value which is a specific activity of a third CDK in the first aliquot, and a sixth specific activity value which is a specific activity of the third CDK in the second aliquot are further acquired,
   in the determination step,
     when the ratio value of the second specific activity value to the first specific activity value is less than a first threshold level, a ratio value of the fourth specific activity value to the third specific activity value is less than a second threshold level, and a ratio value of the sixth specific activity value to the fifth specific activity value is greater than or equal to a third threshold level, or
     when the ratio value of the first specific activity value to the second specific activity value is greater than or equal to the first threshold level, a ratio value of the third specific activity value to the fourth specific activity value is greater than or equal to the second threshold level, and a ratio value of the fifth specific activity value to the sixth specific activity value is less than the third threshold level, the subject is determined to be insensitive to the CDK4/6 inhibitor,
   the first CDK is CDK4, the second CDK is CDK6, and the third CDK is CDK2.

4. A method for determining sensitivity to a CDK4/6 inhibitor of a subject who has been administered the CDK4/6 inhibitor, and treating a cancer in the subject, comprising the steps of:
   acquiring a first specific activity value which is a specific activity of a first CDK in a first sample, and a second specific activity value which is a specific activity of the first CDK in a second sample, wherein the first sample is a sample collected from the subject before administration of the CDK4/6 inhibitor, and the second sample is a sample collected from the subject after administration of the CDK4/6 inhibitor,
   determining that the subject is sensitive to the CDK4/6 inhibitor when a ratio value of the second specific activity value to the first specific activity value is greater than or equal to a predetermined threshold level, or a ratio value of the first specific activity value to the second specific activity value is less than the predetermined threshold level, and
   administering the CDK4/6 inhibitor to the subject determined to be sensitive to the CDK4/6 inhibitor, to treat a cancer in the subject,
   wherein the first CDK is CDK4 or CDK6,
   the first sample is a sample collected from the subject before administration of the CDK4/6 inhibitor, and
   the second sample is a sample collected from the subject after administration of the CDK4/6 inhibitor.

5. The determination method according to claim 4, wherein
   in the acquisition step, a third specific activity value which is a specific activity of a second CDK in the first sample and a fourth specific activity value which is a specific activity of the second CDK in the second sample are further acquired,
   in the determination step,
     when the ratio value of the second specific activity value to the first specific activity value is less than a first threshold level, and a ratio value of the fourth specific activity value to the third specific activity value is greater than or equal to a second threshold level, or
     when the ratio value of the first specific activity value to the second specific activity value is greater than or equal to the first threshold level, and a ratio value of the third specific activity value to the fourth specific activity value is less than the second threshold level, the subject is determined to be insensitive to the CDK4/6 inhibitor, and
   the second CDK is CDK2.

6. The determination method according to claim 4, wherein
   in the acquisition step, a third specific activity value which is a specific activity of a second CDK in the first sample, a fourth specific activity value which is a specific activity of the second CDK in the second sample, a fifth specific activity value which is a specific activity of a third CDK in the first sample, and a sixth specific activity value which is a specific activity of the third CDK in the second sample are further acquired, in the determination step, when the ratio value of the second specific activity value to the first specific activity value is less than a first threshold level, a ratio value of the fourth specific activity value to the third specific activity value is less than a second threshold level, and a ratio value of the sixth specific activity value to the fifth specific activity value is greater than or equal to a third threshold level, or when the ratio value of the first specific activity value to the second specific activity value is greater than or equal to the first threshold level, a ratio value of the third specific activity value to the fourth specific activity value is greater than or equal to the second threshold level, and a ratio value of the fifth specific activity value to the sixth specific activity value is less than the third threshold level, the subject is determined to be insensitive to the CDK4/6 inhibitor, the first CDK is CDK4, the second CDK is CDK6, and the third CDK is CDK2.

7. The determination method according to claim 1, wherein, in the determination step, when the ratio value of the second specific activity value to the first specific activity value is greater than or equal to the predetermined threshold level, or the ratio value of the first specific activity value to the second specific activity value is less than the predetermined threshold level, the subject is determined to be sensitive to the CDK4/6 inhibitor.

8. The method according to claim 1, wherein the subject is a breast cancer patient.

9. The method according to claim 4, wherein the subject is a breast cancer patient.

10. The method according to claim 1, wherein the CDK4/6 inhibitor is palbociclib, abemaciclib, ribociclib, or trilaciclib.

11. The method according to claim 4, wherein the CDK4/6 inhibitor is palbociclib, abemaciclib, ribociclib, or trilaciclib.

12. A method for determining sensitivity of a subject to a CDK4/6 inhibitor, and treating a cancer in the subject, comprising the steps of:

acquiring a first specific activity value which is a specific activity of a first CDK in a first aliquot of a sample collected from a subject, and a second specific activity value which is a specific activity of the first CDK in a second aliquot of the sample, determining that the subject is sensitive to the CDK4/6 inhibitor when a ratio value of the second specific activity value to the first specific activity value is greater than or equal to a predetermined threshold level, or a ratio value of the first specific activity value to the second specific activity value is less than the predetermined threshold level, and administering the CDK4/6 inhibitor to the subject determined to be sensitive to the CDK4/6 inhibitor, to treat a cancer in the subject, wherein the first CDK is CDK4 or CDK6, the first aliquot is an aliquot not treated with the CDK4/6 inhibitor, and the second aliquot is an aliquot treated in vitro with the CDK4/6 inhibitor.

* * * * *